US011686721B2

United States Patent
Takahashi

(10) Patent No.: US 11,686,721 B2
(45) Date of Patent: Jun. 27, 2023

(54) CELL IMAGE ANALYSIS APPARATUS, CELL IMAGE ANALYSIS SYSTEM, METHOD OF GENERATING TRAINING DATA, METHOD OF GENERATING TRAINED MODEL, TRAINING DATA GENERATION PROGRAM, AND METHOD OF PRODUCING TRAINING DATA

(71) Applicant: Shimadzu Corporation, Kyoto (JP)

(72) Inventor: Wataru Takahashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/981,637

(22) PCT Filed: Mar. 20, 2018

(86) PCT No.: PCT/JP2018/011195
§ 371 (c)(1),
(2) Date: Sep. 16, 2020

(87) PCT Pub. No.: WO2019/180848
PCT Pub. Date: Sep. 26, 2019

(65) Prior Publication Data
US 2021/0019499 A1   Jan. 21, 2021

(51) Int. Cl.
*G06V 20/69*   (2022.01)
*G01N 33/483*   (2006.01)
(Continued)

(52) U.S. Cl.
CPC ....... *G01N 33/4833* (2013.01); *G06F 18/214* (2023.01); *G06F 18/285* (2023.01);
(Continued)

(58) Field of Classification Search
CPC combination set(s) only.
See application file for complete search history.

(56) References Cited

U.S. PATENT DOCUMENTS 5,934,278 A * 8/1999 Ishihara ............... A61B 5/0261
600/476
6,246,495 B1   6/2001 Yamaguchi
(Continued)

FOREIGN PATENT DOCUMENTS

JP   10-268740 A   10/1998
JP   2006-517292 A   7/2006
(Continued)

OTHER PUBLICATIONS

Watanabe "Machine learning training data generation (English)" IP.com english translation (Year: 2017).*
(Continued)

*Primary Examiner* — Tsung Yin Tsai
(74) *Attorney, Agent, or Firm* — Muir Patent Law, PLLC

(57) ABSTRACT

A cell image analysis apparatus that can achieve less time and effort for labeling for generation of teaching data than in a conventional example is provided. The cell image analysis apparatus includes an image obtaining unit that obtains a cell image including a removal target that is obtained by a microscope for observation of a cell, a teaching data generator that specifies a removal target region including the removal target within the cell image by performing predetermined image processing and generates as teaching data for machine learning, a label image that represents a location of the removal target region in the cell image, and a training data set generator that generates a set of the cell image and the label image as a training data set to be used in machine learning.

24 Claims, 16 Drawing Sheets

(51) Int. Cl.
  *G06T 7/00* (2017.01)
  *G06F 18/214* (2023.01)
  *G06F 18/20* (2023.01)
  *G06V 10/774* (2022.01)
  *G06V 10/82* (2022.01)

(52) U.S. Cl.
  CPC .......... *G06T 7/0014* (2013.01); *G06V 10/774* (2022.01); *G06V 10/82* (2022.01); *G06V 20/69* (2022.01); *G06T 2207/10056* (2013.01); *G06T 2207/20081* (2013.01); *G06T 2207/20224* (2013.01); *G06T 2207/30024* (2013.01)

(56) References Cited

U.S. PATENT DOCUMENTS

| | | | | |
|---|---|---|---|---|
| 8,935,136 | B2 * | 1/2015 | Smith | G06N 20/00 703/6 |
| 10,572,828 | B2 * | 2/2020 | Crabtree | G06K 9/6256 |
| 11,314,994 | B2 * | 4/2022 | Sato | G06V 10/44 |
| 2006/0139638 | A1 | 6/2006 | Muller et al. | |
| 2006/0280352 | A1 * | 12/2006 | Muschler | G06T 7/0012 382/133 |
| 2011/0124037 | A1 * | 5/2011 | Backhaus | C12M 33/04 435/30 |
| 2011/0228069 | A1 | 9/2011 | Mimura et al. | |
| 2013/0080129 | A1 * | 3/2013 | Smith | G06N 20/00 703/6 |
| 2015/0138334 | A1 * | 5/2015 | Usuba | G02B 21/365 382/134 |
| 2015/0317509 | A1 * | 11/2015 | Kil | G06K 9/6253 382/133 |
| 2016/0314335 | A1 * | 10/2016 | Al-Kofahi | G06V 10/42 |
| 2017/0329281 | A1 | 11/2017 | Tagawa | |
| 2018/0089364 | A1 * | 3/2018 | Muzzey | G16B 40/00 |
| 2018/0197111 | A1 * | 7/2018 | Crabtree | G06K 9/6297 |
| 2018/0268557 | A1 * | 9/2018 | Watanabe | G06T 7/74 |
| 2019/0294107 | A1 | 9/2019 | Kondo et al. | |
| 2020/0160027 | A1 * | 5/2020 | Tsujimoto | G06V 20/695 |
| 2021/0133963 | A1 * | 5/2021 | Takahashi | G06T 7/0012 |

FOREIGN PATENT DOCUMENTS

| | | | | |
|---|---|---|---|---|
| JP | 2009-044974 | A | 3/2009 | |
| JP | 2010-022318 | A | 2/2010 | |
| JP | 2015-210212 | A | 11/2015 | |
| WO | 2016/084420 | A1 | 6/2016 | |
| WO | 2017/203718 | A1 | 11/2017 | |
| WO | 2017/204013 | A1 | 11/2017 | |
| WO | WO-2019039035 | A1 * | 2/2019 | ................ B01L 3/50 |
| WO | WO-2019180848 | A1 * | 9/2019 | ......... G01N 33/4833 |

OTHER PUBLICATIONS

Hertzmann et al "Image Analogies" (Year: 2001).*
First Office Action from the Chinese Intellectual Property Office for corresponding application No. 201880091367.5, dated Mar. 4, 2022.
Japanese Office Action dated Jul. 13, 2021 for the corresponding Japanese Patent Application No. 2020-507194 with a machine translation.
"Cell Culture Analysis System CultureScanner CS-1," Shimadzu Corporation, [searched on Mar. 14, 2018], (URL: https://www.an.shimadzu.co.jp/bio/cell/cs1/index.htm); submitted with a machine translation.
Long et al., "Fully Convolutional Networks for Semantic Segmentation", The IEEE Conference on Computer Vision and Pattern Recognition, 2015, pp. 3431-3440, (URL: https://people.eecs.berkeley.edu/~jonlong/long_shelhamer_fcn.pdf).
Ronneberger et al., "U-NET: Convolutional Networks for Biomedical Image Segmentation", [searched on Mar. 14, 2018], (URL: https://arxiv.org/abs/1505.04597).
Kamishima, "Transfer Leaning", Journal of Japanese Society for Artificial Intelligence, vol. 25, No. 4, Jul. 2010, (URL: https://jsai.ixsq.nii.ac.jp/ej/?action=repository_uri&item_id=7632&file_id=22&file_no=1); submitted with a partial machine translation.
Written Opinion of the International Searching Authority (Form PCT/ISA/237) dated Apr. 24, 2018, for PCT application PCT/JP2018/011195, submitted with a partial machine translation.

* cited by examiner (BEFORE REMOVAL)

(DURING REMOVAL)

(AFTER REMOVAL)

FIG.7

| IDENTIFICATION INFORMATION OF TRAINED MODEL | DATE AND TIME OF CREATION | IDENTIFICATION INFORMATION OF TRAINING DATA SET | OBJECT TO BE IDENTIFIED |
|---|---|---|---|
| TRAINED MODEL A | 2018/3/15 10:00 | TRAINING DATA SET A | FOREIGN MATTER A |
| TRAINED MODEL B | 2018/3/17 14:00 | TRAINING DATA SET B | CELL A |
| TRAINED MODEL C | 2018/3/19 17:00 | TRAINING DATA SET C | CELL B |
| ⋮ | ⋮ | ⋮ | ⋮ |

27A  27B  27C  27D

FIG.8
(A)
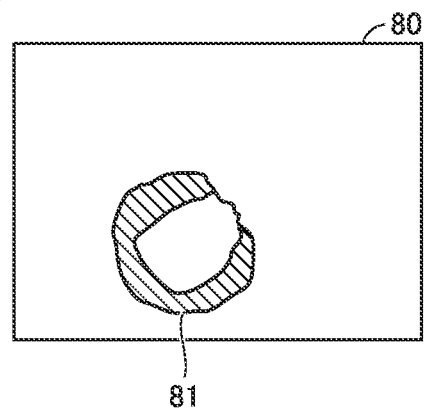
(B)
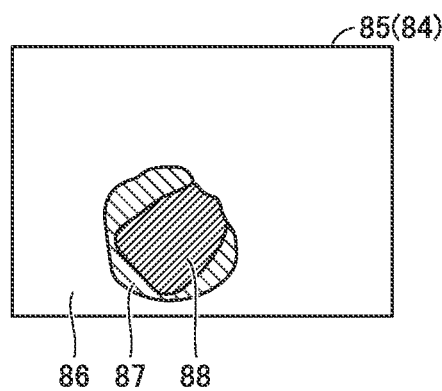

CELL IMAGE ANALYSIS APPARATUS, CELL IMAGE ANALYSIS SYSTEM, METHOD OF GENERATING TRAINING DATA, METHOD OF GENERATING TRAINED MODEL, TRAINING DATA GENERATION PROGRAM, AND METHOD OF PRODUCING TRAINING DATA

TECHNICAL FIELD

The present disclosure relates to a technology for automatically generating teaching data to be used for machine learning.

BACKGROUND ART

In the field of regenerative medicine, researches using pluripotent stem cells such as induced pluripotent stem (iPS) cells or embryonic stem (ES) cells have actively been conducted in recent years. In researches and development of regenerative medicine using such pluripotent stem cells, a large amount of undifferentiated cells should be cultured while their pluripotency is maintained. Therefore, selection of an appropriate culturing environment and stable control of the environment are required and conditions of cells that are being cultured should highly frequently be checked. For example, when cells in a cell colony deviate from an undifferentiated state, all cells within the cell colony finally make transition to a state deviated from the undifferentiated state because they are capable of differentiation in this case. Therefore, an observer should daily check for cells (already differentiated cells or cells about to differentiate, which are referred to as "deviated cells" below) that deviate from the undifferentiated state among cells that are being cultured, and when the observer finds a deviated cell, the observer should promptly remove that cell.

Whether or not pluripotent stem cells maintain the undifferentiated state can reliably be determined by dyeing the cells with an undifferentiation marker. Dyed cells, however, will die, and hence dyeing with an undifferentiation marker cannot be used for determination for pluripotent stem cells for regenerative medicine. At a site of current culturing of cells for regenerative medicine, an observer determines whether or not cells are undifferentiated based on morphological observation of cells with a phase contrast microscope. The phase contrast microscope is used because cells are transparent in general and it is difficult to observe the cells with a common optical microscope.

As disclosed in NPL 1, an apparatus that obtains a cell observation image based on holography has also recently been put into practical use. As disclosed in PTLs 1 to 4, this apparatus creates a phase image in which cells can clearly be observed (which is referred to as an "IHM phase image" below, because in-line holographic microscopy (IHM) is used) by performing data processing such as phase retrieval or image reconstruction onto hologram data obtained by a digital holographic microscope. The digital holographic microscope is advantageous in that phase information at any distance can be calculated in a stage of computation processing after hologram data is obtained and hence focusing at each time of imaging is not required and a time period for measurement can be shorter.

Even though cells can be observed clearly to some extent in a phase contrast micrograph or an IHM phase image, the observer should be skilled to accurately visually determine undifferentiated cells. Since determination is made by a human, variation in determination is inevitable. Therefore, such a conventional approach is not suitable for industrial mass production of pluripotent stem cells.

In order to address the problem, various technologies for evaluation of a condition of cells by processing of a cell observation image have conventionally been proposed.

For example, PTL 5 describes a method of calculating a texture feature value of an intracellular structure from a plurality of cell observation images obtained at prescribed time intervals, computing a difference or a correlation value between the texture feature values of the plurality of cell observation images, and determining a degree of activity of cells based on time-series variation thereof. With this method, for example, when a difference in texture feature value with lapse of time tends to decrease, the degree of activity of the cell can be determined as lowering.

PTL 6 describes a method of predicting quality of cells such as a growth rate, by conducting fuzzy neural network (FNN) analysis with the use of a plurality of index values obtained from a cell observation image. This literature also describes use of a texture feature value found in image processing onto a cell observation image as an index value.

Other than FNN analysis, application of various learning approaches to cell biology has been proposed. For example, NPL 2 discloses a learning approach relating to fully convolutional neural networks FCN. NPL 3 discloses an approach to application of the FCN to cell biology. NPL 4 discloses a learning approach relating to transfer learning.

CITATION LIST

Patent Literature

PTL 1: WO2017/203718
PTL 2: WO2017/204013
PTL 3: WO2016/084420
PTL 4: Japanese Patent Laying-Open No. 10-268740
PTL 5: Japanese Patent Laying-Open No. 2010-022318
PTL 6: Japanese Patent Laying-Open No. 2009-044974

Non Patent Literature

NPL 1: "Cell Culture Analysis System CultureScanner CS-1," [online], Shimadzu Corporation, [searched on Mar. 14, 2018], the Internet <URL: https://www.an.shimadzu.co.jp/bio/cell/csl/index.htm>
NPL 2: Jonathan Long et al., "Fully Convolutional Networks for Semantic Segmentation," The IEEE Conference on Computer Vision and Pattern Recognition, 2015, pp. 3431-3440, (the Internet <URL: https://people.eecs.berkeley.edu/~jonlong/long_shelhamer_fcn.pdf>)
NPL 3: Olaf Ronneberger, Philipp Fischer, Thomas Brox, "Convolutional Networks for Biomedical Image Segmentation," U-Net, [searched on Mar. 14, 2018], (the Internet <URL: https://arxiv.org/abs/1505.04597>)
NPL 4: Toshihiro Kamishima, "Transfer Leaning," Journal of Japanese Society for Artificial Intelligence, Vol. 25, No. 4, July 2010, (the Internet <URL: https://j sai.ixsq.nii.ac.jp/ej/?action=repository_uri&item_id=7632&file_id=22&file_no=1>)

SUMMARY OF INVENTION

Technical Problem

An observer should remove a removal target such as a deviated cell or an impurity from an observed target in order to maintain an appropriate culturing environment. Learning of such a removal target by machine learning to allow automatic identification of the removal target in an image of one or more cells (which may be referred to as a "cell image" or "cellular image" herein) obtained by imaging of an observed object by a microscope has been desired. In order to realize this machine learning, a designer should manually label a region including a removal target in a large number of cell images and prepare results of labeling as teaching data. Since labeling for a large number of cell images requires much time and effort, reduction in time and effort for labeling has been desired.

Solution to Problem

In one example of the present disclosure, a cell image analysis apparatus capable of generating teaching data to be used for machine learning includes an image obtaining unit that obtains a first cell image including a removal target, the first cell image being obtained by a microscope for observation of a cell, a teaching data generator that specifies a removal target region including the removal target within the first cell image by performing predetermined image processing and generates as the teaching data for machine learning, a label image that represents a location of the removal target region within the first cell image, and a training data set generator that generates a set of the first cell image and the label image as a training data set to be used for machine learning.

According to this disclosure, the cell image analysis apparatus automatically generates a training data set of a label image as teaching data and a cell image from which the label image has originated. As such a scheme is provided, a designer does not have to label the cell image in collecting training data.

In one example of the present disclosure, the image obtaining unit further obtains a second cell image obtained by the microscope after removal of the removal target. The predetermined image processing includes specifying the removal target region based on a result of comparison between the first cell image and the second cell image.

According to this disclosure, the cell image analysis apparatus can more accurately specify the removal target region including the removal target based on comparison between images before and after removal of the removal target.

In one example of the present disclosure, the predetermined image processing includes specifying the removal target region based on a subtraction image obtained by subtracting the second cell image from the first cell image.

According to this disclosure, as the subtraction image of images before and after removal of the removal target is used, the cell image analysis apparatus can further accurately specify the removal target region including the removal target.

In one example of the present disclosure, the cell image analysis apparatus further includes a removal mechanism that removes an object included in a predetermined region within the first cell image. The predetermined image processing includes specifying the predetermined region within the first cell image as the removal target region.

According to this disclosure, the cell image analysis apparatus can specify the removal target region including the removal target with a more simplified method.

In one example of the present disclosure, the cell image analysis apparatus includes a trained-model generator that carries out machine learning using a plurality of training data sets generated by the training data set generator and generates a trained model for identifying the removal target within an image and a detector that detects the removal target region in an input image input to the cell image analysis apparatus based on the trained model.

According to this disclosure, as the trained model generated from the collected training data set is used, the removal target region is automatically detected in the input image.

In one example of the present disclosure, machine learning carried out by the trained-model generator includes transfer learning using as an initial model, a part or the entirety of the trained model trained in advance.

According to this disclosure, the cell image analysis apparatus can converge various parameters within the trained model in an early stage.

In one example of the present disclosure, the cell image analysis apparatus further includes a storage device that stores a plurality of trained models generated by the trained-model generator and an input portion that accepts a selection operation to select one trained model from among the plurality of trained models. The detector detects the removal target region in the input image based on the trained model selected by the selection operation.

According to this disclosure, an observer can switch the trained model in accordance with a type or an application of the removal target.

In one example of the present disclosure, the cell image analysis apparatus further includes a display and a display processing unit that causes the display to show the removal target region detected by the detector as being superimposed on the input image.

According to this disclosure, the observer can readily check the location of the removal target region in the input image.

In one example of the present disclosure, the cell image analysis apparatus includes a removal mechanism controller that controls the removal mechanism of the microscope to remove the removal target based on a result of detection of the removal target region detected by the detector.

According to this disclosure, time and effort for looking for a removal target are saved and a removal operation does not have to be performed.

In another example of the present disclosure, a cell image analysis system capable of generating teaching data to be used for machine learning includes a server and a plurality of cell image analysis apparatuses that communicate with the server. The plurality of cell image analysis apparatuses each include an image obtaining unit that obtains a cell image including a removal target, the cell image being obtained by a microscope for observation of a cell, a teaching data generator that specifies a removal target region including the removal target within the cell image by performing predetermined image processing and generates as the teaching data for machine learning, a label image that represents a location of the removal target region within the cell image, a training data set generator that generates a set of the cell image and the label image as a training data set to be used for machine learning, and a communication unit that transmits the training data set to the server.

According to this disclosure, the server can collect from each cell image analysis apparatus, a training data set of a label image as teaching data and a cell image from which the label image has originated. As such a scheme is provided, a designer can readily collect a large number of training data sets.

In another example of the present disclosure, a method includes receiving a cell image and a label image that represents a location of a removal target region within the cell image, generating, by carrying out machine learning using the received cell image and label image, a trained model that uses the cell image as an input image and provides an image that represents a location of a removal target region within the input image as an output image, and transmitting the generated trained model.

According to this disclosure, a trained model for automatically detecting a removal target region in an input image is generated.

In another example of the present disclosure, a method of generating teaching data to be used for machine learning includes obtaining a cell image including a removal target, the cell image being obtained by a microscope for observation of a cell, specifying a removal target region including the removal target within the cell image by performing predetermined image processing and generating as the teaching data for machine learning, a label image that represents a location of the removal target region within the cell image, and generating a set of the cell image and the label image as a training data set to be used for machine learning.

According to this disclosure, a training data set of a label image as teaching data and a cell image from which the label image has originated is automatically generated. As such a scheme is provided, a designer does not have to label the cell image in generating training data.

In another example of the present disclosure, a generation program that generates teaching data to be used for machine learning causes a computer to perform obtaining a cell image including a removal target, the cell image being obtained by a microscope for observation of a cell, specifying a removal target region including the removal target within the cell image by performing predetermined image processing and generating as the teaching data for machine learning, a label image that represents a location of the removal target region within the cell image, and generating a set of the cell image and the label image as a training data set to be used for machine learning.

According to this disclosure, a training data set of a label image as teaching data and a cell image from which the label image has originated is automatically generated. As such a scheme is provided, a designer does not have to label the cell image in generating training data.

In another example of the present disclosure, a method of producing teaching data to be used for machine learning includes obtaining a cell image including a removal target, the cell image being obtained by a microscope for observation of a cell, specifying a removal target region including the removal target within the cell image by performing predetermined image processing and generating as the teaching data for machine learning, a label image that represents a location of the removal target region within the cell image, and generating a set of the cell image and the label image as a training data set to be used for machine learning.

According to this disclosure, a training data set of a label image as teaching data and a cell image from which the label image has originated is automatically generated. As such a scheme is provided, a designer does not have to label the cell image in generating training data.

BRIEF DESCRIPTION OF DRAWINGS

FIG. 7 is a diagram showing an exemplary data structure of a database of a trained model.

FIG. 8 is a diagram showing an exemplary result of display implemented by a display processing unit.

DESCRIPTION OF EMBODIMENTS

Figure 1:
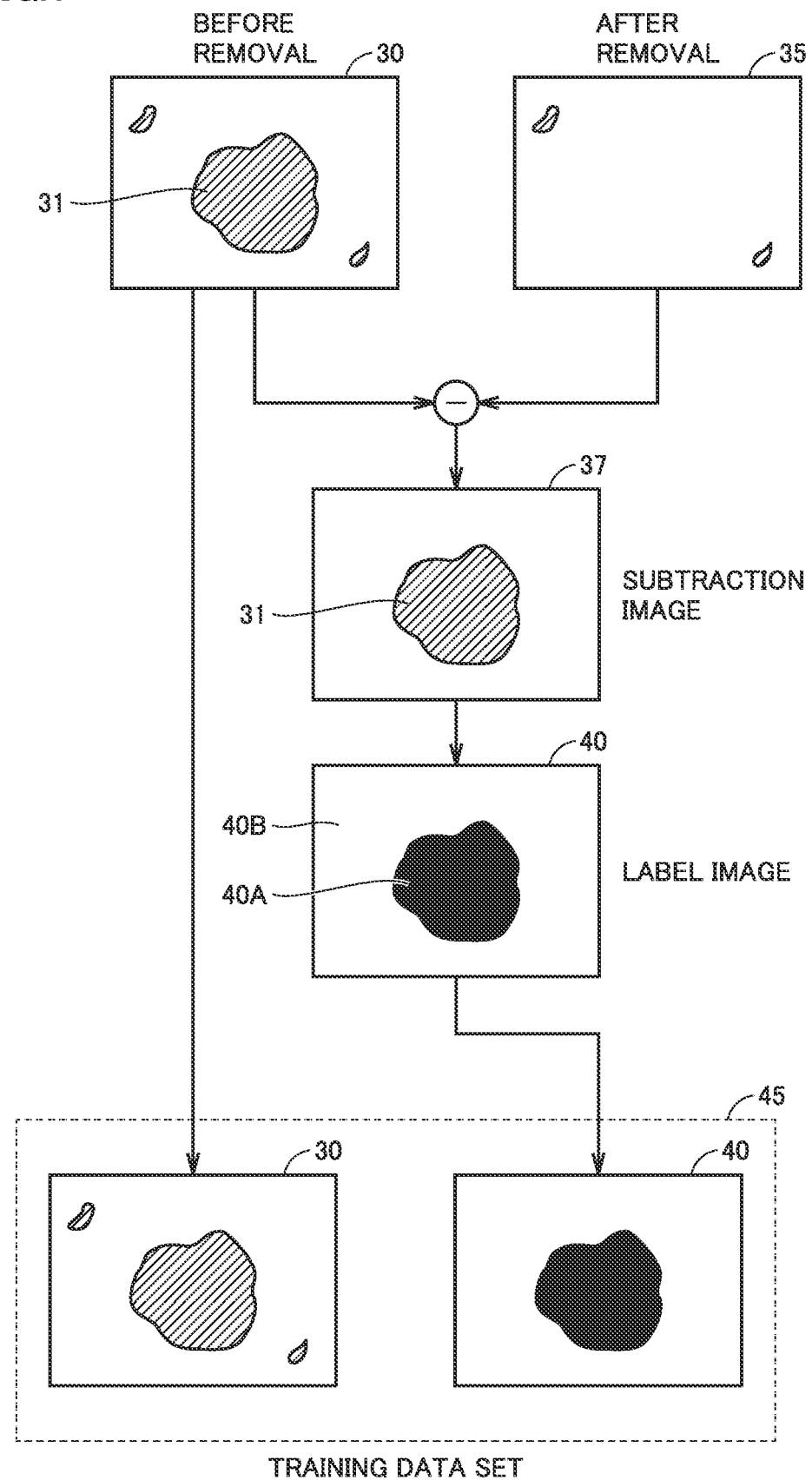
FIG. 1 is a conceptual diagram schematically showing a process of generation of a training data set in a first embodiment.

Each embodiment according to the present invention will be described below with reference to the drawings. In the description below, the same elements and components have the same reference characters allotted and their labels and functions are also the same. Therefore, detailed description thereof will not be repeated.

Each embodiment and each modification described below may selectively be combined as appropriate.

First Embodiment

<1. Overview>

An observer should remove a removal target such as a deviated cell or an impurity from an observed target in order to maintain an appropriate culturing environment. In order to generate a trained model for automatically identifying such a removal target, a designer should prepare a large number of cell images including removal targets and prepare label images in which a removal target region within each cell image is labeled as training data. A cell image analysis apparatus 1 (see FIG. 2) according to the present embodiment automatically generates such a label image as teaching data and outputs a training data set of the label image and the cell image.

More specifically, by performing predetermined image processing for specifying a removal target region onto a cell image (a first cell image), cell image analysis apparatus 1 specifies a removal target region within the cell image and generates a label image that represents a location of the removal target region within the cell image. Thereafter, cell image analysis apparatus 1 outputs a set of the cell image and the label image as a training data set to be used for machine learning. As the label image is thus automatically generated, manual labeling of a cell image does not have to be performed.

A method of generating a training data set will specifically be described below with reference to FIG. 1. FIG. 1 is a conceptual diagram schematically showing a process of generation of a training data set.

FIG. 1 shows cell images 30 and 35 obtained by imaging of an observed object such as a cell by a microscope. Cell image 30 (a first cell image) is an image obtained by imaging of an observed object before removal of a removal target 31. Cell image 35 (a second cell image) is an image obtained by imaging of an observed object after removal of removal target 31.

Cell image analysis apparatus 1 performs predetermined image processing onto cell images 30 and 35 to specify a removal target region that represents removal target 31. Predetermined image processing for specifying a removal target region includes specifying a removal target region based on a result of comparison between cell image 30 before removal of removal target 31 and cell image 35 after removal of removal target 31.

By way of example, cell image analysis apparatus 1 specifies a removal target region based on a subtraction image obtained by subtraction of cell image 35 from cell image 30. More specifically, cell image analysis apparatus 1 subtracts cell image 35 from cell image 30 to generate a subtraction image 37. Each pixel value of subtraction image 37 corresponds to a difference between pixel values at a coordinate identical between cell images 30 and 35. By subtracting cell image 35 after removal of removal target 31 from cell image 30 before removal of removal target 31, only removal target 31 is extracted in subtraction image 37.

Thereafter, cell image analysis apparatus 1 binarizes subtraction image 37 based on a predetermined threshold value. By way of example, cell image analysis apparatus 1 allocates a first value (for example, 255) to a pixel of which value exceeds a predetermined threshold value and allocates a second value (for example, 0) to a pixel of which value is equal to or smaller than the predetermined threshold value. By such binarization, a label image 40 in which a removal target region 40A and a non-removal target region 40B are labeled is generated. Typically, label image 40 is equal in size to cell image 30 and each pixel value of label image 40 indicates whether or not a corresponding pixel (identical pixel) of cell image 30 falls under a removal target region.

Cell image analysis apparatus 1 associates label image 40 that represents a location of removal target 31 within cell image 30 with cell image 30 from which label image 40 has originated, and generates such images as a training data set 45. As such training data sets 45 are successively generated, training data sets 45 are accumulated.

As set forth above, cell image analysis apparatus 1 specifies removal target region 40A based on cell image 30 before removal of removal target 31 and cell image 35 after removal of removal target 31 and generates label image 40 that represents a location of removal target region 40A as teaching data. As such label image 40 is automatically generated, a designer can collect a large amount of teaching data without labeling a cell image.

Though description is given above on the premise that label image 40 is a binarized image, label image 40 does not necessarily have to be a binarized image. By way of example, label image 40 may be labeled in accordance with a type of a removal target. More specifically, a predetermined pixel value (number) is allocated for each type of a removal target, and as a designer designates a type of a removal target for extracted removal target region 40A, a pixel value in accordance with the designated type is allocated to removal target region 40A. In such a case, each pixel value of label image 40 indicates the type of removal target 31.

Though an example in which removal target region 40A is specified based on subtraction image 37 between cell image 30 before removal of removal target 31 and cell image 35 after removal of removal target 31 is described above, processing for specifying removal target region 40A is not limited as such. By way of example, in processing for specifying removal target region 40A, a predetermined region within cell image 30 before removal of removal target 31 may be specified as removal target region 40A.

More specifically, depending on a type, some microscopes are provided with a removal mechanism (for example, a removal mechanism 17 which will be described later). By way of example of a manner of use of the removal mechanism, an observer looks for a removal target in an observed object while the observer checks a cell image shown as a through-the-lens image. When the observer finds the removal target, the observer moves the observed object or an imaging portion such that the removal target is included in a predetermined region (for example, at the center) of the cell image and then performs a removal operation onto cell image analysis apparatus 1. The removal mechanism removes an object located in the predetermined region of the cell image based on acceptance of a removal operation. When such a microscope is used, a location where a removal target is included is not varied for each image. With attention being paid to this fact, cell image analysis apparatus 1 obtains cell image 35 imaged at the time of or immediately before acceptance of the removal operation, and specifies the predetermined region in cell image 35 as removal target region 40A.

<2. Configuration of Cell Image Analysis Apparatus 1>

Figure 2:
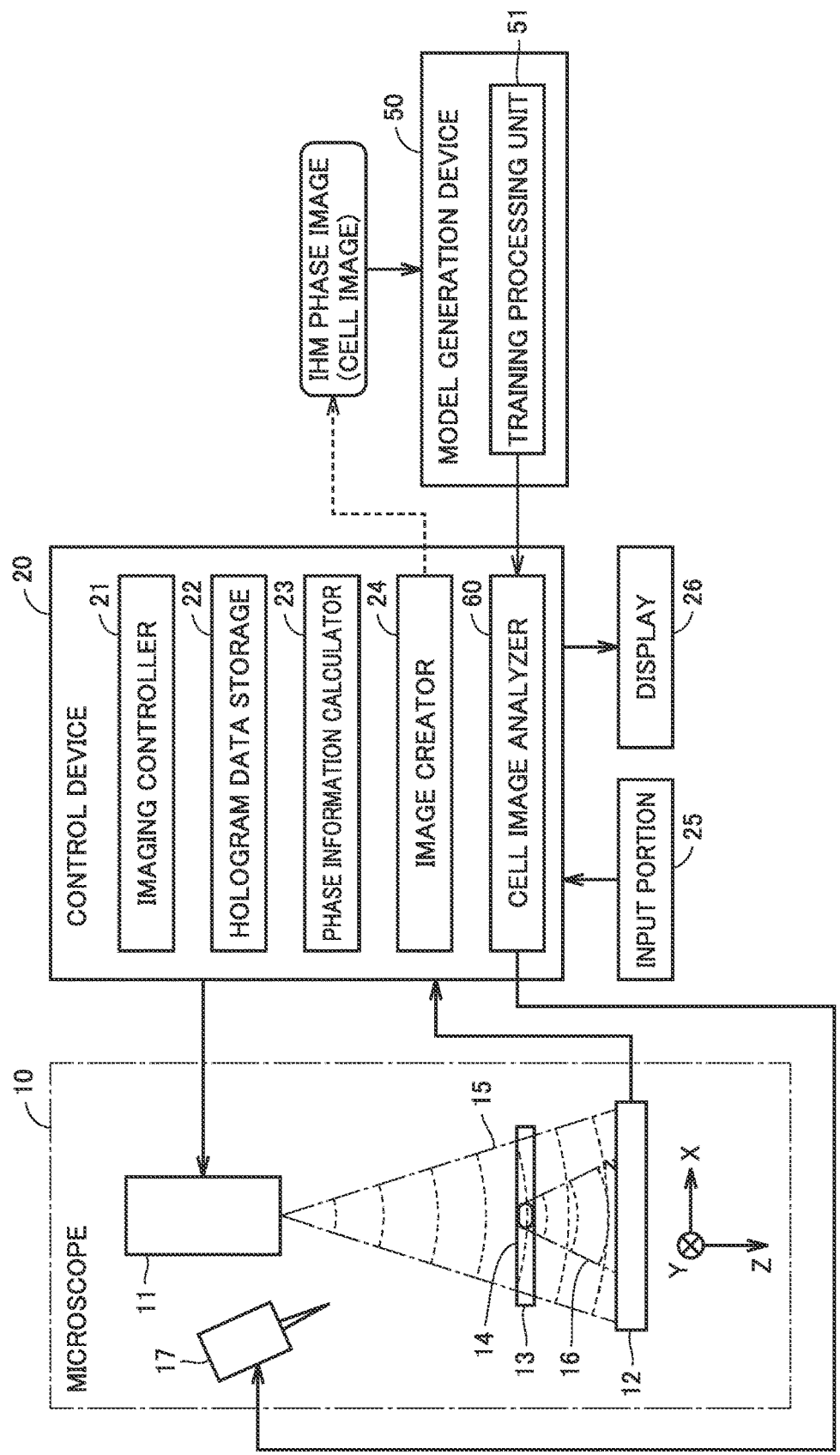
FIG. 2 is a diagram showing a schematic configuration of a cell image analysis apparatus according to the first embodiment.

A configuration of cell image analysis apparatus 1 according to the present embodiment will be described with reference to FIG. 2. FIG. 2 is a diagram showing a schematic configuration of cell image analysis apparatus 1 according to the present embodiment.

Cell image analysis apparatus 1 in the present example includes a microscope 10, a control device 20, an input portion 25 serving as a user interface, a display 26, and a model generation device 50.

Microscope 10 is an in-line holographic microscope (IHM) and includes a light source 11 including a laser diode, an image sensor 12, and removal mechanism 17. A culture plate 13 containing a cell colony (or a cell alone) 14 is arranged between light source 11 and image sensor 12.

Control device 20 controls operations of microscope 10, processes data obtained by microscope 10, and includes an imaging controller 21, a hologram data storage 22, a phase information calculator 23, an image creator 24, and a cell image analyzer 60 as functional blocks.

Normally, an entity of control device 20 is a personal computer in which prescribed software has been installed or a slightly more sophisticated work station, or a computer system including a sophisticated computer connected to such a computer through a communication line. A function of each block included in control device 20 can be performed by processing using various types of data stored in the computer or the computer system, the processing being performed by execution of software mounted on the computer alone or the computer system including a plurality of computers.

An entity of model generation device 50 is also a personal computer in which prescribed software has been installed or a more sophisticated work station. Though this computer is normally a computer different from control device 20, it may be the same as the control device. In other words, control device 20 can also perform the function of model generation device 50.

Initially, operations and processing until creation of an IHM phase image which is an observation image used in segmentation of cells in cell image analysis apparatus 1 in the present example will be described.

When an operator sets culture plate 13 containing cell colony 14 at a prescribed position and performs a prescribed operation through input portion 25, imaging controller 21 controls microscope 10 to obtain hologram data as below.

Light source 11 emits coherent light that spreads by a small angle around 10° to a prescribed region of culture plate 13. Coherent light (object light 16) that has passed through culture plate 13 and cell colony 14 reaches image sensor 12 while it interferes with light (reference light 15) that has passed through a region proximate to cell colony 14 on culture plate 13. Object light 16 has its phase varied in passage through cell colony 14, whereas reference light is free from phase variation due to colony 14 because it does not pass through cell colony 14. Therefore, on a detection surface (an image surface) of image sensor 12, an image resulting from interference fringes between object light 16 having a phase varied by cell colony 14 and reference light 15 having a phase unchanged is formed.

Light source 11 and image sensor 12 are successively moved in an X-axis direction and a Y-axis direction by a not-shown movement mechanism. A region irradiated with coherent light (an observed region) emitted from light source 11 is moved over culture plate 13 and hologram data over a wide two-dimensional region (two-dimensional light intensity distribution data of a hologram formed on the detection surface of image sensor 12) can be obtained.

Hologram data obtained by microscope 10 as described above is successively sent to control device 20 and stored in hologram data storage 22. In control device 20, phase information calculator 23 reads the hologram data from hologram data storage 22 and calculates phase information of the entire observed region (imaged region) by performing prescribed computation processing for phase retrieval. Image creator 24 creates an IHM phase image based on the calculated phase information. In calculation of such phase information or creation of the IHM phase image, a well-known algorithm disclosed in PTLs 3 and 4 may be used. Phase information calculator 23 may calculate not only phase information but also intensity information or pseudo phase information together based on the hologram data, and image creator 24 may create a reconstruction image, that is, an intensity image or a pseudo phase image, based on such information.

Figure 3:
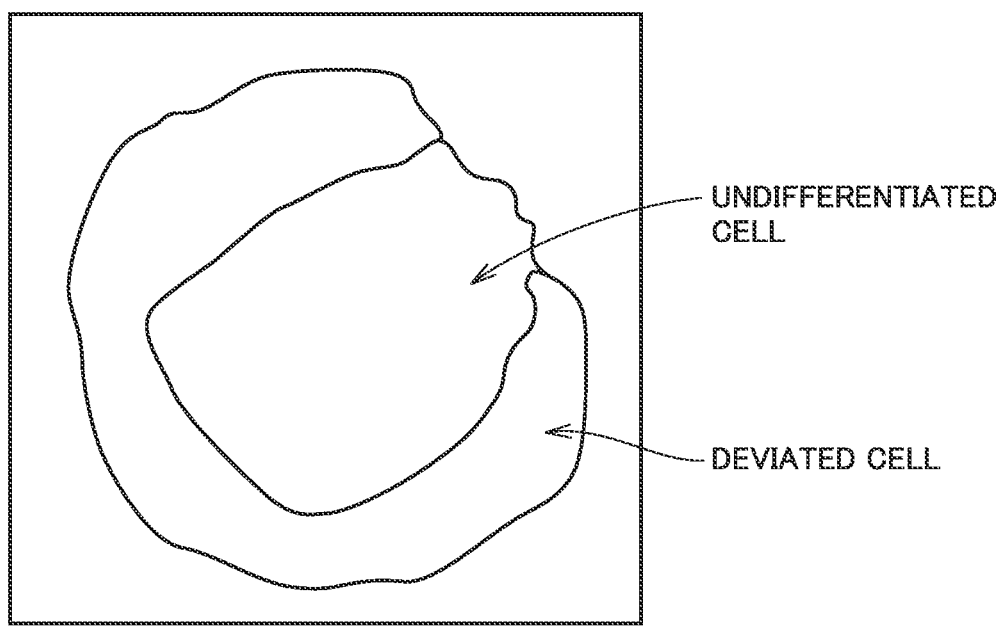
FIG. 3 is a diagram showing one example (a deviated cell colony) of an IHM phase image.

FIG. 3 shows an exemplary IHM phase image of a deviated cell colony in an iPS cell. Typical characteristics of a deviated cell have been known to "thinly spread," and based on these characteristics, a region of an undifferentiated cell and a region of a deviated cell can visually be recognized also in FIG. 3. Though an operator experienced to some extent could identify a region of an undifferentiated cell and a region of a deviated cell by looking at such an image, operations for visual inspection of a large number of IHM phase images one by one for identification impose large burden. For an image of which identification is more difficult, a result of identification may often be different among operators. In contrast, cell image analysis apparatus 1 according to the present embodiment can automatically identify an undifferentiated cell region and a deviated cell region by segmentation of an IHM phase image using the fully convolutional neural network representing one of machine learning methods. Details of the fully convolutional neural network will be described later.

Removal mechanism 17 removes an object located in a predetermined region on culture plate 13 in accordance with a control instruction from control device 20. Removal mechanism 17 may be a laser mechanism that removes a removal target by irradiation with laser or a suction mechanism that removes a removal target by suction. Removal mechanism 17 as the laser mechanism removes a removal target by emitting near infrared laser beams to cause cells in an irradiated portion to come off. Removal mechanism 17 as the suction mechanism includes a pipet called a tip. An observer of microscope 10 moves culture plate 13 or the pipet such that a removal target is located at the center of image sensor 12 and suctions the removal target thereon.

<3. Functional Configuration for Realizing Machine Learning>

Figure 4:
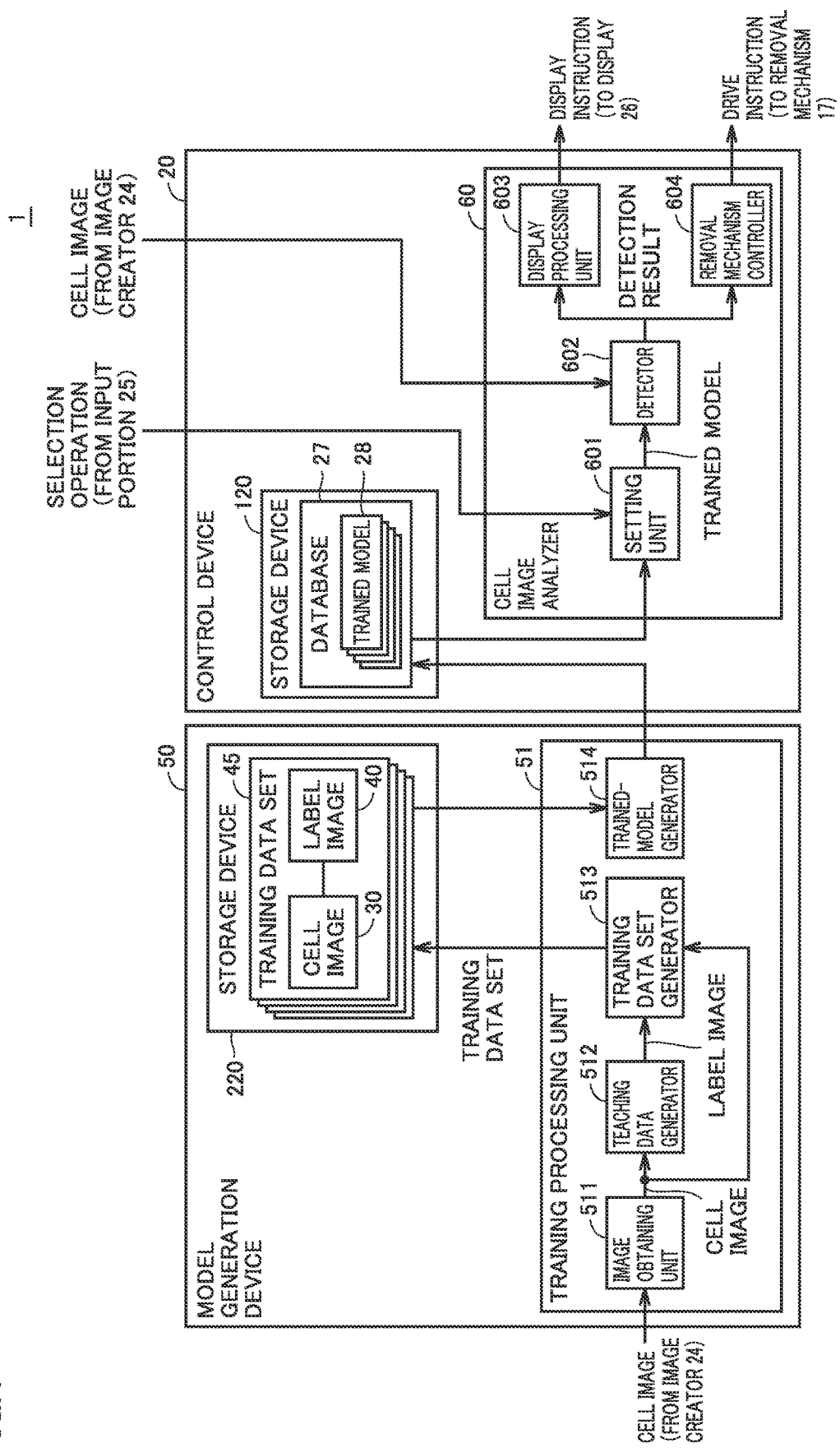
FIG. 4 is a diagram showing an exemplary functional configuration for realizing machine learning in the first embodiment.

A main functional configuration for realizing machine learning will be described with reference to FIGS. 4 to 8. FIG. 4 is a diagram showing an exemplary functional configuration for realizing machine learning.

As shown in FIG. 4, cell image analysis apparatus 1 includes control device 20 and model generation device 50. Control device 20 includes a cell image analyzer 60 which is a functional module and a storage device 120 which is a piece of hardware. Model generation device 50 includes a training processing unit 51 which is a functional module and a storage device 220 which is a piece of hardware.

Training processing unit 51 includes an image obtaining unit 511, a teaching data generator 512, a training data set generator 513, and a trained-model generator 514 as functional modules. Cell image analyzer 60 includes a setting unit 601, a detector 602, a display processing unit 603, and a removal mechanism controller 604.

A function of each functional module of training processing unit 51 and cell image analyzer 60 will sequentially be described below.

(3.1. Image Obtaining Unit 511)

A function of image obtaining unit 511 will initially be described.

Image obtaining unit 511 obtains at least cell image 30 before removal of a removal target from image creator 24 (see FIG. 2) described above. Preferably, image obtaining unit 511 further obtains cell image 35 after removal of the removal target.

Figure 5:
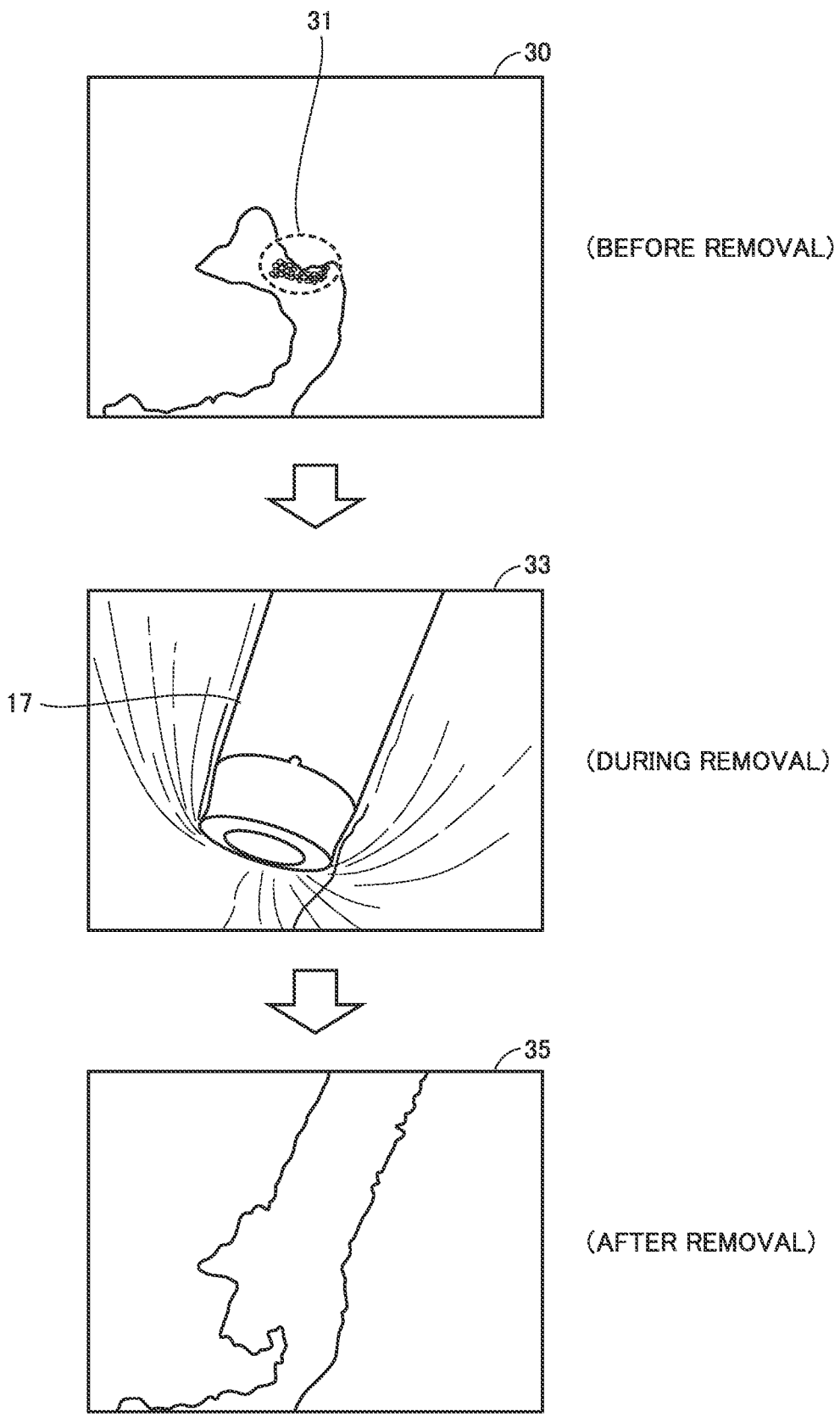
FIG. 5 is a diagram showing a process for removing a removal target in the first embodiment.

FIG. 5 is a diagram showing a process for removing a removal target. More specifically, FIG. 5 shows cell image 30 obtained before removal of removal target 31, a cell image 33 obtained during removal of removal target 31 by removal mechanism 17, and cell image 35 obtained after removal of removal target 31. Image obtaining unit 511 obtains cell images 30 and 35 before and after removal of the removal target, among these images.

Whether or not current time is before removal of removal target 31 is determined, for example, based on whether or not an observer has performed a removal operation through input portion 25 described above. More specifically, image obtaining unit 511 obtains as cell image 30 before removal, an image received at the time when input portion 25 (see FIG. 2) described above has accepted the removal operation. Alternatively, image obtaining unit 511 obtains as cell image 30 before removal, an image received within a prescribed time period (for example, one second) immediately before acceptance of the removal operation by input portion 25.

Whether or not current time is after removal of removal target 31 is determined, for example, based on whether or not removal processing by removal mechanism 17 has been completed. More specifically, image obtaining unit 511 obtains as cell image 35 after removal, an image received at the time of acceptance of a signal indicating completion of removal processing by removal mechanism 17 from removal mechanism controller 604. Alternatively, image obtaining unit 511 obtains as cell image 35 after removal, an image received within a prescribed time period (for example, one second) immediately after acceptance of a signal indicating completion of removal processing by removal mechanism 17 from removal mechanism controller 604.

Image obtaining unit 511 outputs cell images 30 and 35 before and after removal of the removal target to teaching data generator 512 and outputs cell image 30 before removal of the removal target to training data set generator 513.

A method of obtaining cell images 30 and 35 before and after removal of the removal target is not limited to the method described above. For example, cell images 30 and 35 before and after removal of the removal target may be selected by an operation by a user. In this case, as an observer selects two cell images from among cell images shown as being arranged on a time-series basis, cell images 30 and 35 before and after removal of the removal target are obtained.

(3.2. Teaching Data Generator 512)

A function of teaching data generator 512 shown in FIG. 4 will now be described.

By performing predetermined training processing on cell image 30 received from image obtaining unit 511, teaching data generator 512 specifies a removal target region including a removal target within cell image 30 and generates as teaching data, label image 40 representing a position of the removal target region. Since the method of generating label image 40 is as described with reference to FIG. 1, description thereof will not be repeated.

In label image 40, at least a removal target region and a non-removal target region are distinguished. By way of example, to a pixel representing the removal target region, a first value (for example, any of 1 to 255) is allocated as a pixel value. To a pixel representing the non-removal target region, a second value (for example, 0) is allocated as a pixel value.

Preferably, a pixel value in accordance with a type of the removal target is allocated to a pixel representing the removal target region. More specifically, a predetermined pixel value (number) is allocated for each type of the removal target, and as a designer designates a type of the removal target in the removal target region, a pixel value in accordance with the designated type is allocated to the removal target region.

Teaching data representing the type of the removal target is thus generated. As such teaching data is used for machine learning, not only a location of the removal target region can be specified but also a trained model allowing identification of the type of the removal target can be generated.

Label image 40 generated by teaching data generator 512 is output to training data set generator 513.

(3.3. Training Data Set Generator 513)

A function of training data set generator 513 shown in FIG. 4 will now be described.

Training data set generator 513 associates cell image 30 obtained by image obtaining unit 511 with label image 40 as teaching data generated from cell image 30, and generates the associated images as training data set 45. Generated training data set 45 is stored in storage device 220 each time it is generated. Training data sets 45 are thus accumulated in storage device 220.

Preferably, training data set generator 513 has a check screen shown for checking whether or not to store training data set 45 in storage device 220, before storage of training data set 45 in storage device 220. Training data set generator 513 has storage device 220 store training data set 45 based on issuance of an instruction to store training data set 45 to the check screen. Training data set generator 513 otherwise discards training data set 45.

(3.4. Trained-Model Generator 514)

A function of trained-model generator 514 shown in FIG. 4 will now be described.

Trained-model generator 514 carries out machine learning using a plurality of training data sets 45 generated by training data set generator 513 and generates a trained model for identification of a removal target within a cell image. A learning approach adopted by trained-model generator 514 is not particularly limited, and various types of machine learning such as deep learning including the fully convolutional neural network (FCN) and support vector machine can be adopted.

Figure 6:
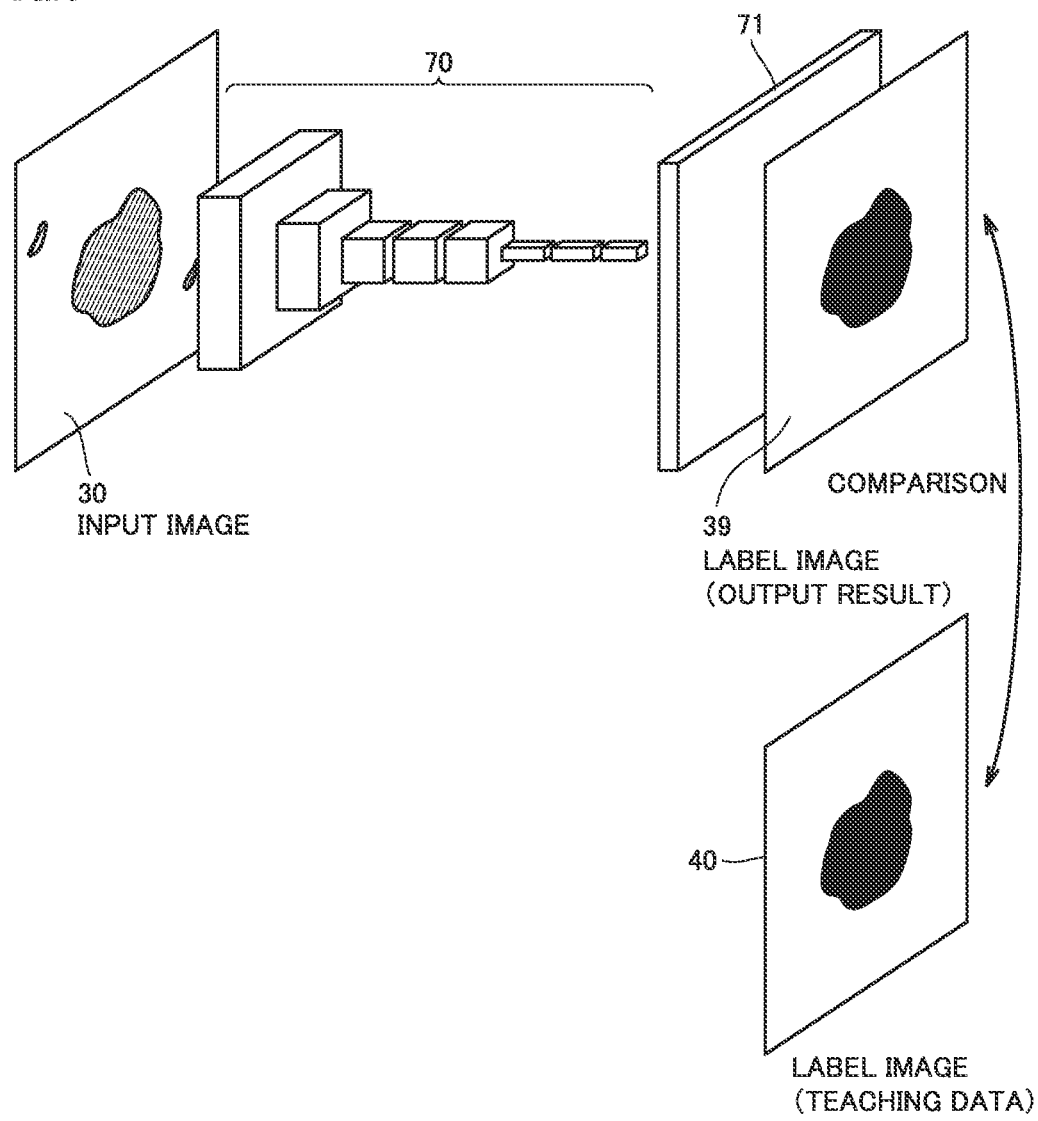
FIG. 6 is a conceptual diagram showing a structure of a fully convolutional neural network.

The fully convolutional neural network will be described below by way of example of the learning approach with reference to FIG. 6. FIG. 6 is a conceptual diagram of a structure of the fully convolutional neural network. Details of the structure of or processing by the fully convolutional neural network are described in many literatures including NPL 2. Implementation utilizing commercially available or free software such as "MATLAB" provided by MathWorks in the United States can also be made. Therefore, brief description is given here.

As shown in FIG. 6, the fully convolutional neural network includes a multi-layered network 70 in which multiple layers, for example, of convolutional layers and pooling layers are repeatedly layered and a convolutional layer 71 corresponding to the fully connected layer in the convolutional neural network. In this case, in multi-layered network 70, convolution processing using a filter (kernel) of a prescribed size and pooling processing for two-dimensionally scaling down results of convolution to extract an effective value are repeated. Multi-layered network 70 may be constituted only of convolutional layers without pooling layers. In convolutional layer 71 in the final stage, local convolution and deconvolution are carried out while the filter of the prescribed size is slid within an input image. In the fully convolutional neural network, a label image 39 in which a removal target region and a non-removal target region are labeled can be output by segmentation of cell image 30 such as an IHM phase image.

In order to identify a very small foreign matter such as dust introduced during culturing of cells, multi-layered network 70 and convolutional layer 71 are designed to label an input IHM phase image for each pixel thereof. A minimum unit of one region labeled in label image 39 which is an output image is one pixel in the IHM phase image. Therefore, for example, even when a foreign matter having a size as large as one pixel is observed in the IHM phase image, that foreign matter is detected as one region in label image 39 and information on where the foreign matter is located can accurately be provided to an operator.

Trained-model generator 514 inputs cell image 30 included in training data set 45 into the fully convolutional neural network and compares consequently output label image 39 with label image 40 as teaching data associated with cell image 30. Trained-model generator 514 updates various parameters within multi-layered network 70 and convolutional layer 71 such that label image 39 as an output result is closer to label image 40 as teaching data. As such updating processing is repeated for all training data sets 45, various parameters within multi-layered network 70 and convolutional layer 71 are optimized. Various parameters that have been optimized are output to control device 20 as a trained model 28. The various parameters include, for example, a value or a weight of each filter applied in the convolutional layer of multi-layered network 70.

Generated trained models 28 are accumulated in a database 27 in storage device 120 of control device 20. FIG. 7 is a diagram showing an exemplary data structure of database 27.

Database 27 includes identification information 27A for identification of a trained model, information 27B on date and time of creation of the trained model, identification information 27C for identification of a training data set from which a trained model has originated, and identified object information 27D that defines an object to be identified by a trained model.

Identification information 27A of a trained model is defined, for example, by a name of the trained model or an identification (ID). Identification information 27C of a training data set is defined, for example, by a name of the training data set or a path to a folder where the training data set is stored. Identified object information 27D is defined by a name of a cell or a name of a foreign matter.

Transfer learning using some or all of other trained models trained in another environment as an initial model may be used in machine learning by trained-model generator 514. Transfer learning refers to a technology for adapting a trained model trained in one environment to another environment.

More specifically, trained-model generator 514 applies some or all of other trained models trained in another environment as an initial value of various parameters within multi-layered network 70 and convolutional layer 71, and then carries out machine learning described above. Through such transfer learning, various parameters within multi-layered network 70 and convolutional layer 71 converge in an early stage. Even though there are few training data sets 45, a trained model high in accuracy in identification is generated.

(3.5. Setting Unit 601)

A function of setting unit 601 shown in FIG. 4 will now be described.

Setting unit 601 sets in detector 602, one trained model selected from among trained models defined in database 27. A selection operation to select a trained model is performed, for example, through input portion 25 described above.

More specifically, an observer invokes a screen for setting a trained model and has display 26 of cell image analysis apparatus 1 show the setting screen. In the setting screen, trained models included in database 27 are shown in a list. Various types of information defined in database 27 are shown as being aligned with trained models. Various types of information include, for example, identification information 27A of a trained model (see FIG. 7), information 27B on date and time of creation of the trained model (see FIG. 7), identification information 27C of a training data set from which the trained model has originated (see FIG. 7), and identified object information 27D for identification based on the trained model (see FIG. 7).

A designer selects one trained model from among the trained models shown in the list by operating input portion 25. Setting unit 601 sets the selected trained model in detector 602, based on selection of the trained model.

The observer can thus select any trained model defined in database 27. The observer can thus switch a trained model in accordance with a type or an application of a removal target.

(3.6. Detector 602)

A function of detector 602 shown in FIG. 4 will now be described.

Detector 602 detects a removal target region in an input image newly input to cell image analysis apparatus 1 based on trained model 28 set by setting unit 601. Detector 602 may perform detection processing on cell images successively obtained from image creator 24 each time, or for each part of an input image by scanning the input image.

Detector 602 outputs a label image in which a removal target region and a non-removal target region are distinguished, as a result of detection. Meaning by each pixel value in the label image as the result of detection is varied depending on a set trained model.

By way of example, when a trained model that identifies two classes of the removal target region and the non-removal target region has been set, each pixel value of the label image as the result of detection is expressed by a binary number. By way of example, a pixel having a value "255 (or 1)" is regarded as the removal target region and a pixel having a value "0" is regarded as the non-removal target region.

In another example, when a trained model that identifies three or more classes such as a type of the removal target and a type of the non-removal target has been set, each pixel value of the label image as the result of detection is expressed by a value in accordance with the number of identified classes. Each pixel value of the label image as the result of detection represents the type of the class. Relation between each class and the pixel value is defined in advance.

The result of detection by detector 602 is output to display processing unit 603 and removal mechanism controller 604.

(3.7. Display Processing Unit 603)

A function of display processing unit 603 shown in FIG. 4 will now be described.

Display processing unit 603 has display 26 of cell image analysis apparatus 1 show a removal target region detected by detector 602. FIG. 8 is a diagram showing an exemplary result of display implemented by display processing unit 603.

FIG. 8 (A) shows a display result 80 in an example where two-class classification trained model that identifies a removal target region and a non-removal target region is applied to an input image. In display result 80, the detected removal target region is indicated by a marker 81. Display processing unit 603 thus has display 26 show a removal target region detected by detector 602 as being superimposed on the input image.

FIG. 8 (B) shows a label image 84 as a display result 85 in an example where a three-class classification trained model that identifies a background, a deviated cell, and an undifferentiated cell is applied to an input image. In display result 85, an image area 86 representing the background, an image area 87 representing a deviated cell, and an image area 88 representing an undifferentiated cell are colored differently. Image area 87 representing the deviated cell is shown as a removal target region, and image areas 86 and 88 representing the background and the undifferentiated cell are shown as the non-removal target region.

A manner of display of the display result implemented by display processing unit 603 is not limited to the example in FIG. 8. For example, display processing unit 603 may have a message shown as being superimposed on an input image, the message indicating presence of a removal target region.

(3.8. Removal Mechanism Controller 604)

A function of removal mechanism controller 604 shown in FIG. 4 will now be described.

Removal mechanism controller 604 controls removal mechanism 17 to remove a removal target based on a result of detection of the removal target region by detector 602. More specifically, removal mechanism controller 604 transforms a removal target region expressed in a microscope coordinate system into a coordinate expressed in a world coordinate system, based on detection of the removal target region by detector 602. A matrix of transformation from the microscope coordinate system into the world coordinate system is defined in advance. Removal mechanism controller 604 has removal mechanism 17 driven to move to a removal position resulting from transformation into the world coordinate system, and then sends a removal instruction to removal mechanism 17. Removal mechanism 17 starts removal processing based on acceptance of the removal instruction.

Removal mechanism controller 604 thus controls removal mechanism 17 to automatically remove the removal target based on a result of detection of the removal target region by detector 602. Time and effort for looking for a removal target are thus saved and a removal operation does not have to be performed. Furthermore, as such a scheme for automatic removal is provided, quality control during culturing of cells can be automated.

<4. Hardware Configuration>

Figure 9:
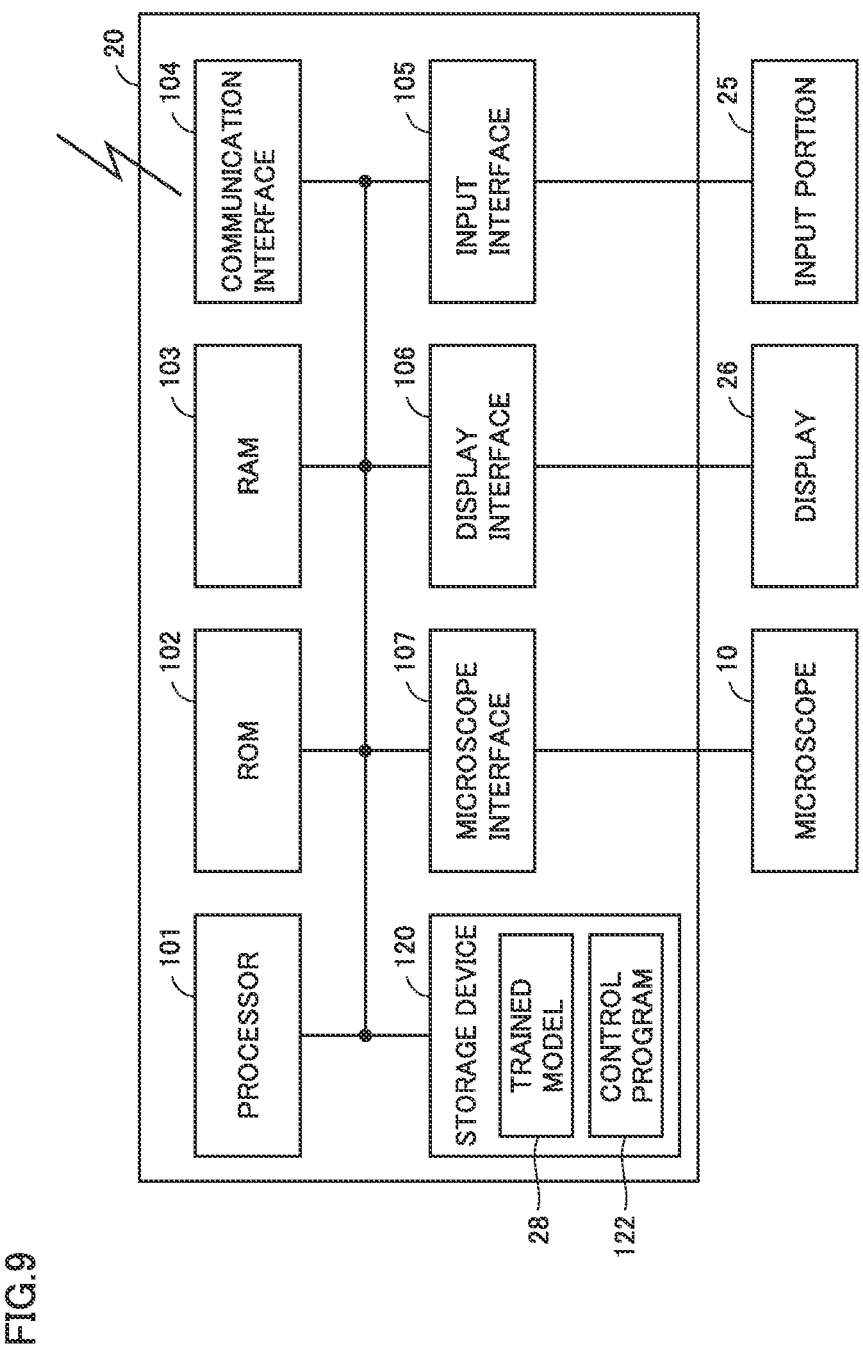
FIG. 9 is a block diagram showing a main hardware configuration of a control device according to the first embodiment.
Figure 10:
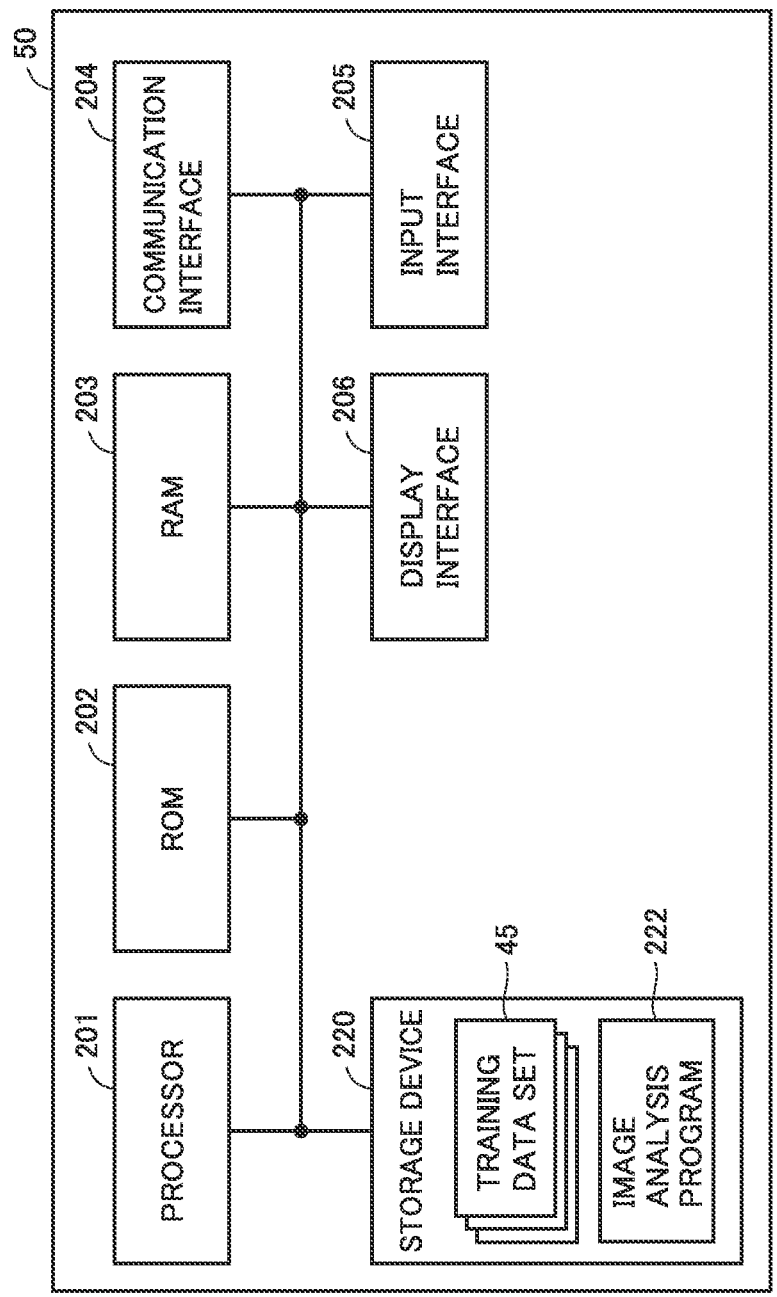
FIG. 10 is a block diagram showing a main hardware configuration of a model generation device according to the first embodiment.

Hardware of control device 20 and model generation device 50 implemented in cell image analysis apparatus 1 will sequentially be described with reference to FIGS. 9 and 10.

(4.1. Hardware Configuration of Control Device 20)

An exemplary hardware configuration of control device 20 will initially be described with reference to FIG. 9. FIG. 9 is a block diagram showing a main hardware configuration of control device 20.

Control device 20 includes a processor 101, a read only memory (ROM) 102, a random access memory (RAM) 103, a communication interface 104, an input interface 105, a display interface 106, a microscope interface 107, and a storage device 120.

Processor 101 is implemented, for example, by at least one integrated circuit. The integrated circuit is implemented, for example, by at least one central processing unit (CPU), at least one application specific integrated circuit (ASIC), at least one field programmable gate array (FPGA), or combination thereof.

Processor 101 controls an operation of control device 20 by executing various programs such as a control program 122 of microscope 10. Processor 101 reads control program 122 from storage device 120 to ROM 102 based on acceptance of an instruction to execute control program 122. RAM 103 functions as a working memory and temporarily stores various types of data necessary for execution of control program 122.

A LAN or an antenna is connected to communication interface 104. Control device 20 exchanges data with an external communication apparatus through communication interface 104. The external communication apparatus includes, for example, a server (for example, a server 300 which will be described later) and other communication terminals. Control device 20 may download control program 122 from a server.

Input interface 105 is implemented, for example, by a universal serial bus (USB) terminal and connected to input portion 25. Input interface 105 accepts a signal indicating an operation by a user from input portion 25. Input portion 25 is implemented, for example, by a mouse, a keyboard, a touch panel, or other input devices capable of accepting an operation by the user.

Display interface 106 is connected to display 26 and sends an image signal for display of an image to display 26 in response to a command from processor 101. Display 26 is implemented, for example, by a liquid crystal display, an organic EL display, or another display apparatus. Display 26 shows, for example, a result of detection of a removal target region by cell image analysis apparatus 1 or various setting screens for cell image analysis apparatus 1.

Storage device 120 is implemented, for example, by a storage medium such as a hard disk or a flash memory. Storage device 120 stores trained model 28 generated by model generation device 50 or control program 122 for microscope 10. A location where trained model 28 and control program 122 are stored is not limited to storage device 120 but the trained model and the control program may be stored in a storage area of processor 101 (for example, a cache memory), ROM 102, RAM 103, or an external apparatus (for example, a server).

(4.2. Hardware Configuration of Model Generation Device 50)

An exemplary hardware configuration of model generation device 50 will now be described with reference to FIG. 10. FIG. 10 is a block diagram showing a main hardware configuration of model generation device 50.

Model generation device 50 includes a processor 201, a ROM 202, a RAM 203, a communication interface 204, an input interface 205, a display interface 206, a microscope interface 207, and a storage device 220. Such hardware is the same as the hardware of control device 20 and as described with reference to FIG. 9 above. Therefore, only difference from control device 20 will be described below.

Storage device 220 is implemented, for example, by a storage medium such as a hard disk or a flash memory. Storage device 220 stores training data set 45 collected for generation of a trained model and an image analysis program 222 for performing various types of processing relating to training processing. Image analysis program 222 includes a generation program for generation of a training data set. A location where training data set 45 and image analysis program 222 are stored is not limited to storage device 220 but the training data set and the image analysis program may be stored in a storage area of processor 201 (for example, a cache memory), ROM 202, RAM 203, or an external apparatus (for example, a server).

Image analysis program 222 may be provided as being incorporated in a part of any program, rather than a single program alone. In this case, processing according to the present embodiment is performed in cooperation with any program. Even such a program not including some modules does not depart from the gist of image analysis program 222 according to the present embodiment. A part or the entirety of functions provided by image analysis program 222 may be performed by dedicated hardware.

Control device 20 and model generation device 50 may execute image analysis program 222 in cooperation.

<5. Control Structure>

Main processing relating to training processing performed by cell image analysis apparatus 1 includes (a) processing for collecting training data sets, (b) training processing using collected training data sets, and (c) detection processing for detecting a removal target region in an input image based on the trained model generated by training processing.

Such processing (a) to (c) is performed by execution of a program by processor 101 of control device 20 or processor 201 of model generation device 50. In another aspect, a part or the entirety of processing may be performed by a circuit element or other hardware.

Processing (a) to (c) will sequentially be described below with reference to FIGS. 11 to 13.

(5.1. Processing for Collecting Training Data Sets)

A flow of processing for collecting training data sets will initially be described with reference to FIG. 11. FIG. 11 is a flowchart showing processing for collecting training data sets. Collection processing shown in FIG. 11 is performed, for example, by processor 201 of model generation device 50.

In step S110, processor 201 determines whether or not an operation mode of model generation device 50 has been set to a mode of automatic collection of training data sets. The automatic collection mode is set, for example, in response to an operation by a user. When processor 201 determines that the operation mode of model generation device 50 has been set to the automatic collection mode (YES in step S110), it switches control to step S120. Otherwise (NO in step S110), processor 201 quits collection processing shown in FIG. 11.

In step S120, processor 201 determines whether or not it has sensed a removal operation onto microscope 10. The removal operation is distinguished based on an operation by the user through input portion 25 (see FIG. 2) described above. When processor 201 determines that it has sensed the removal operation onto microscope 10 (YES in step S120), it switches control to step S122. Otherwise (NO in step S120), processor 201 returns control to step S110.

In step S122, processor 201 as image obtaining unit 511 (see FIG. 4) described above obtains cell image 30 before removal of a removal target and cell image 35 after removal of the removal target. Since the method of obtaining cell images 30 and 35 is as described in "3.1. Image Obtaining Unit 511," description thereof will not be repeated.

In step S124, processor 201 as teaching data generator 512 (see FIG. 4) described above specifies removal target region 40A in cell images 30 and 35 obtained in step S122 and generates label image 40 that represents a location of removal target region 40A within the cell images as teaching data. Since the method of generating label image 40 is as described in "3.2. Teaching Data Generator 512," description thereof will not be repeated.

In step S126, processor 201 as training data set generator 513 (see FIG. 4) described above generates cell image 30 obtained in step S122 and label image 40 generated in step S124 as training data set 45 to be used in machine learning. Since the method of generating training data set 45 is as described in "3.3. Training Data Set Generator 513," description thereof will not be repeated.

Removal target region 40A is specified based on cell images 30 and 35 obtained in step S122, and label image 40 representing the location of removal target region 40A within the cell images is generated as teaching data. Since the method of generating label image 40 is as described in "3.2. Teaching Data Generator 512," description thereof will not be repeated.

Figure 11:
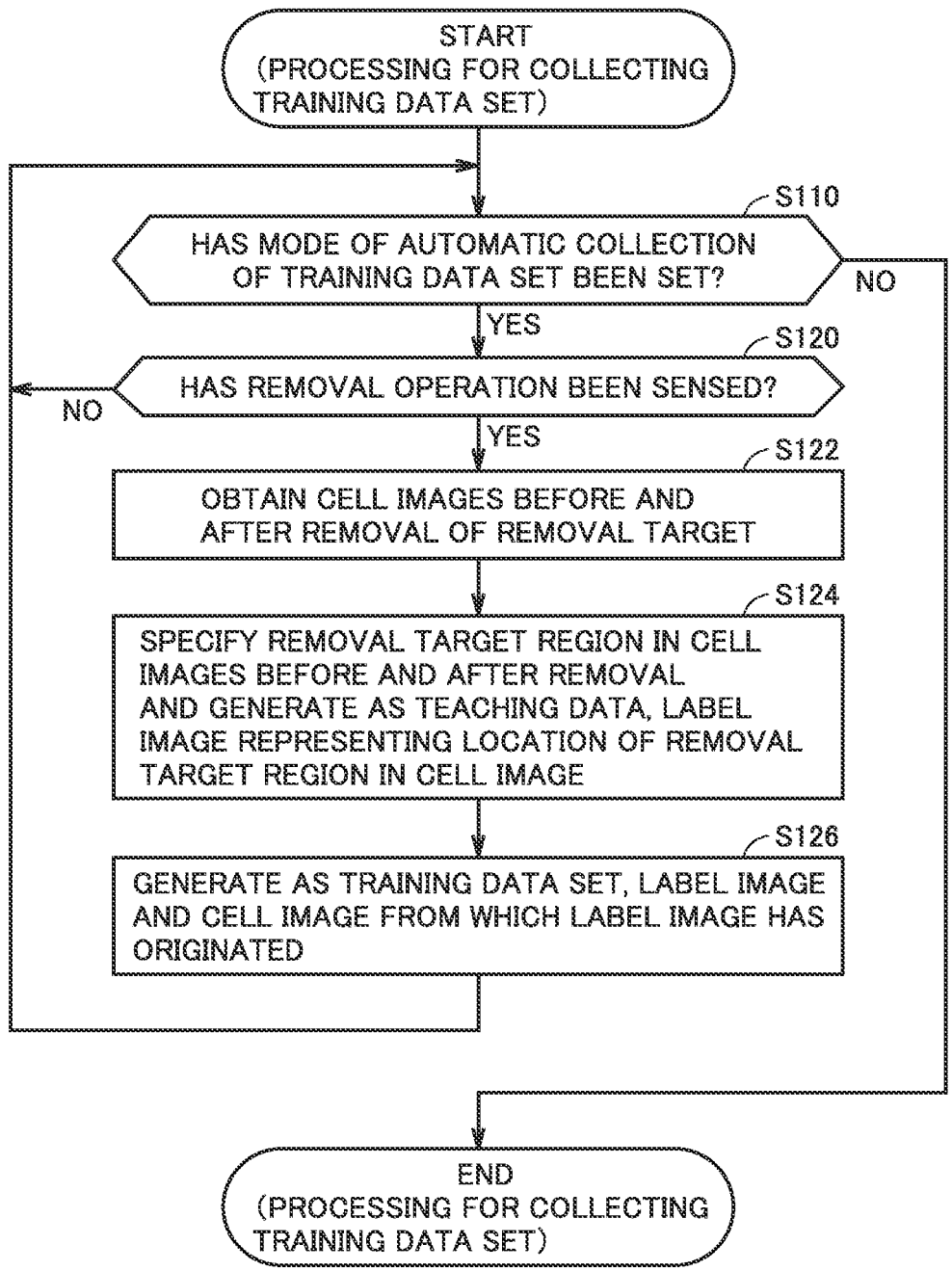
FIG. 11 is a flowchart showing processing for collecting training data sets.

As processing in each step shown in FIG. 11 is repeated as set forth above, training data sets are accumulated.

(5.2. Training Processing)

Processing for training data sets collected in collection processing described above will now be described with reference to FIG. 12. FIG. 12 is a flowchart showing processing for training collected training data sets. Training processing shown in FIG. 12 is performed, for example, by processor 201 of model generation device 50.

In step S210, processor 201 determines whether or not training processing has been performed. When processor 201 determines that training processing has been performed (YES in step S210), it switches control to step S212. Otherwise (NO in step S210), processor 201 performs processing in step S210 again.

In step S212, processor 201 obtains one untrained training data set 45 or a plurality of untrained training data sets 45 among the plurality of training data sets stored in storage device 220.

In step S214, processor 201 as trained-model generator 514 (see FIG. 4) described above applies cell image 30 included in training data set 45 obtained in step S212 to a current trained model.

In step S216, processor 201 as trained-model generator 514 described above compares label image 39 obtained from the current trained model as a result of application in step S214 with label image 40 as teaching data included in training data set 45 obtained in step S212. Then, processor 201 updates various parameters within the current trained model such that label image 39 as the result of application is closer to label image 40 as teaching data.

In step S220, processor 201 determines whether or not there is an untrained training data set among the training data sets stored in storage device 220. When processor 201 determines that there is an untrained training data set (YES in step S220), it quits training processing shown in FIG. 12. Otherwise (NO in step S220), processor 201 returns control to step S212.

Figure 12:
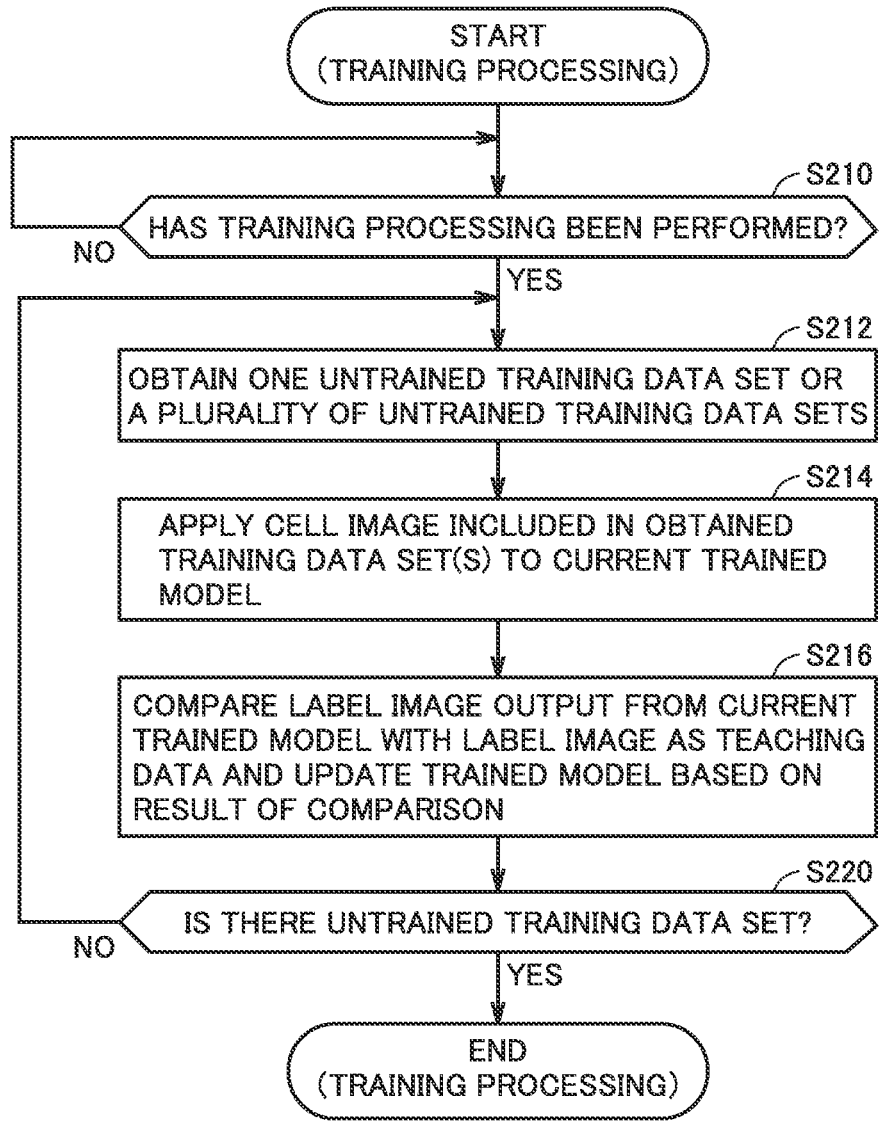
FIG. 12 is a flowchart showing processing for training collected training data sets.
Figure 13:
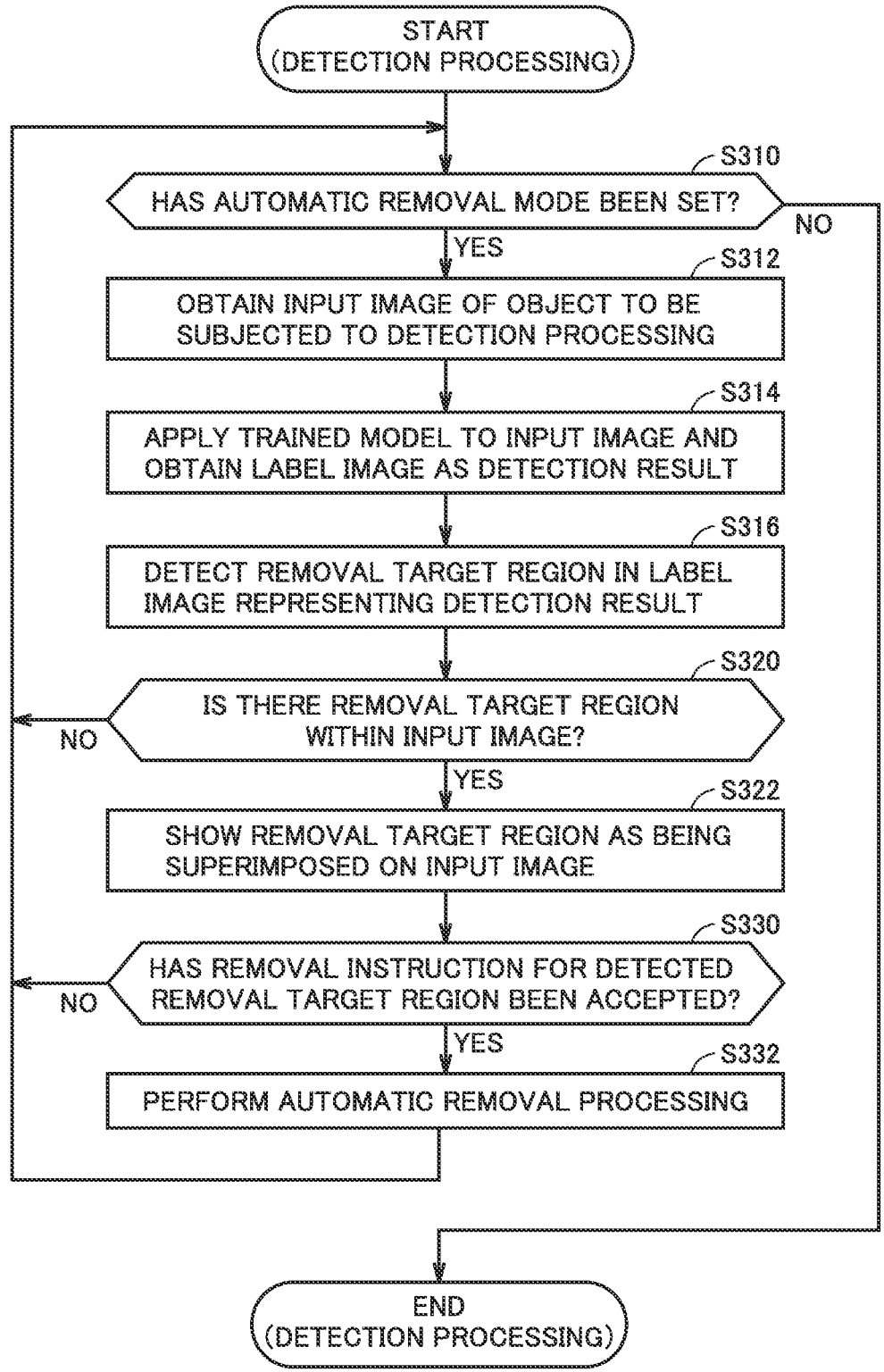
FIG. 13 is a flowchart showing detection processing for detecting a removal target region in an input image.

As steps S212, S214, S216, and S220 shown in FIG. 12 are repeated as set forth above, various parameters that define the trained model are successively updated in conformity with the teaching data.

(5.3. Detection Processing)

Processing for detecting a removal target region in an input image based on a trained model generated in training processing described above will now be described with reference to FIG. 13. FIG. 13 is a flowchart showing detection processing for detecting a removal target region in an input image. Detection processing shown in FIG. 13 is performed, for example, by processor 101 of control device 20.

In step S310, processor 101 determines whether or not the operation mode of control device 20 has been set to an automatic removal mode. The automatic removal mode is set, for example, in response to an operation by a user. When processor 101 determines that the operation mode of control device 20 has been set to the automatic removal mode (YES in step S310), it switches control to step S312. Otherwise (NO in step S310), processor 101 quits detection processing shown in FIG. 13.

In step S312, processor 101 carries out imaging of an object to be inspected such as a cell and obtains an input image as an IHM phase image from image creator 24 (see FIG. 2).

In step S314, processor 101 applies the trained model obtained in the training processing in FIG. 12 described above to the input image obtained in step S312 and obtains label image 84 as a result of detection.

In step S316, processor 101 as detector 602 (see FIG. 4) described above specifies the removal target region based on label image 84 obtained in step S314. By way of example, processor 101 groups a set of pixels each having a value indicating the removal target region and calculates an area (for example, the number of pixels) for each group. When there is a group having an area not smaller than a prescribed value, processor 101 determines that there is a removal target region within the input image.

In step S320, when processor 101 determines that there is a removal target region within the input image (YES in step S320), it switches control to step S322. Otherwise (NO in step S320), processor 201 returns control to step S310.

In step S322, processor 101 as display processing unit 603 (see FIG. 4) described above has display 26 show the removal target region detected in step S316 as being superimposed on the input image. Since the method of showing the removal target region is as described in "3.7. Display Processing Unit 603," description thereof will not be repeated.

In step S330, processor 101 determines whether or not it has accepted a removal instruction for removing the detected removal target region. The removal instruction is issued, for example, based on an operation by a user through input portion 25 described above. When processor 101 determines that it has accepted the removal instruction for removing the detected removal target region (YES in step S330), it switches control to step S332. Otherwise (NO in step S330), processor 201 returns control to step S310.

In step S332, processor 101 as removal mechanism controller 604 (see FIG. 4) described above has removal mechanism 17 of microscope 10 driven to remove the removal target based on a position (a coordinate value) of the removal target region detected in step S316. Since the method of removal is as described in "3.8. Removal Mechanism Controller 604," description thereof will not be repeated.

<6. Summary of First Embodiment>

As set forth above, cell image analysis apparatus 1 according to the present embodiment specifies removal target region 40A in cell image 30 including a removal target and generates as teaching data, label image 40 that represents a location of removal target region 40A within cell image 30. Cell image analysis apparatus 1 then generates generated label image 40 and cell image 30 from which the label image has originated as training data set 45 to be used for machine learning.

Since label image 40 as teaching data is thus automatically generated, a designer does not have to label cell image 30. Consequently, time for collection of training data is significantly reduced. Since such a scheme for automatic generation of a training data set is provided, the designer can readily collect a large number of training data sets.

Second Embodiment

<7. Overview>

In the first embodiment described above, a function to collect training data sets and a function to train the collected training data sets are performed in cell image analysis apparatus 1. In contrast, such functions are performed in a server in a second embodiment.

Since the hardware configuration of cell image analysis apparatus 1 is otherwise as described in the first embodiment above, description thereof will not be repeated below.

<8. System Configuration>

Figure 14:
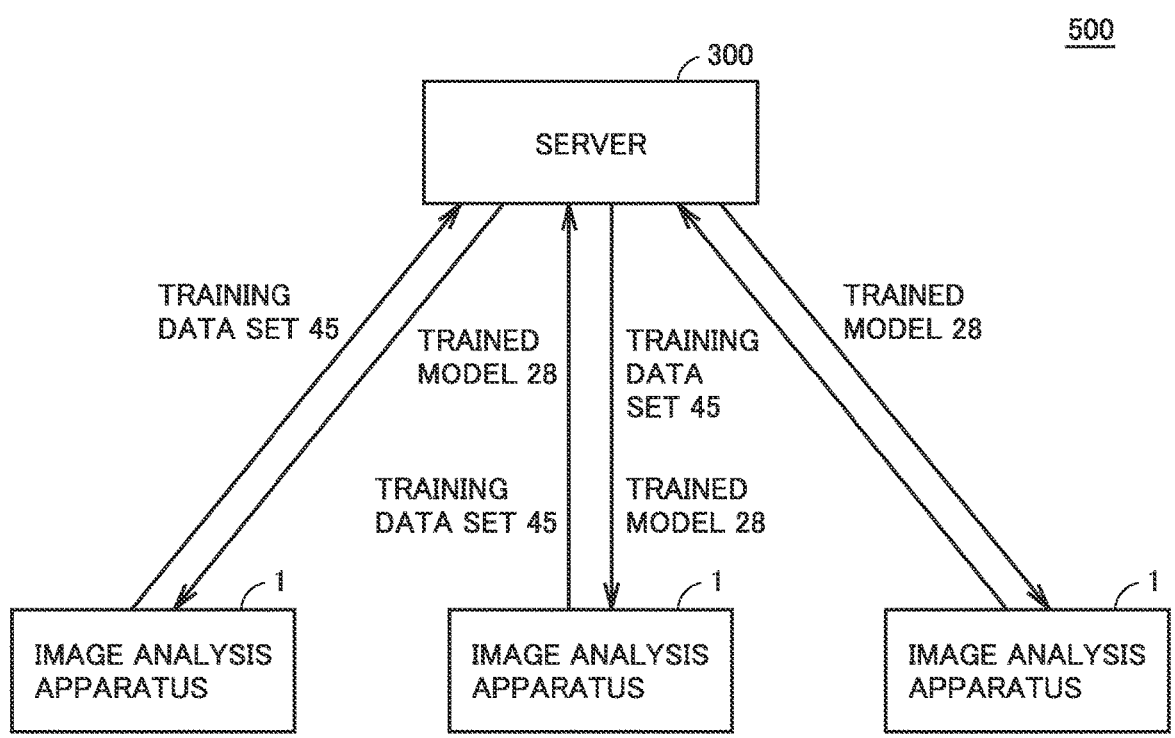
FIG. 14 is a diagram showing an exemplary system configuration of a cell image analysis system according to a second embodiment.

A system configuration of a cell image analysis system 500 according to the second embodiment will be described with reference to FIG. 14. FIG. 14 is a diagram showing an exemplary system configuration of cell image analysis system 500 according to the second embodiment.

As shown in FIG. 14, cell image analysis system 500 includes a plurality of cell image analysis apparatuses 1 and at least one server 300. Each of cell image analysis apparatuses 1 and server 300 can communicate with each other.

Each of cell image analysis apparatuses 1 generates training data set 45 with the method described in the "first embodiment" above. Generated training data set 45 is transmitted to server 300. Server 300 accumulates training data sets 45 received from cell image analysis apparatuses 1. Server 300 then carries out machine learning described above of collected training data sets 45 and generates a trained model. The generated trained model is distributed to each of cell image analysis apparatuses 1.

Though FIG. 14 shows an example in which cell image analysis system 500 includes three cell image analysis apparatuses 1, cell image analysis system 500 should only include at least one cell image analysis apparatus 1. Though FIG. 14 shows an example in which cell image analysis system 500 includes one server 300, cell image analysis system 500 may include a plurality of servers 300.

<9. Functional Configuration>

Figure 15:
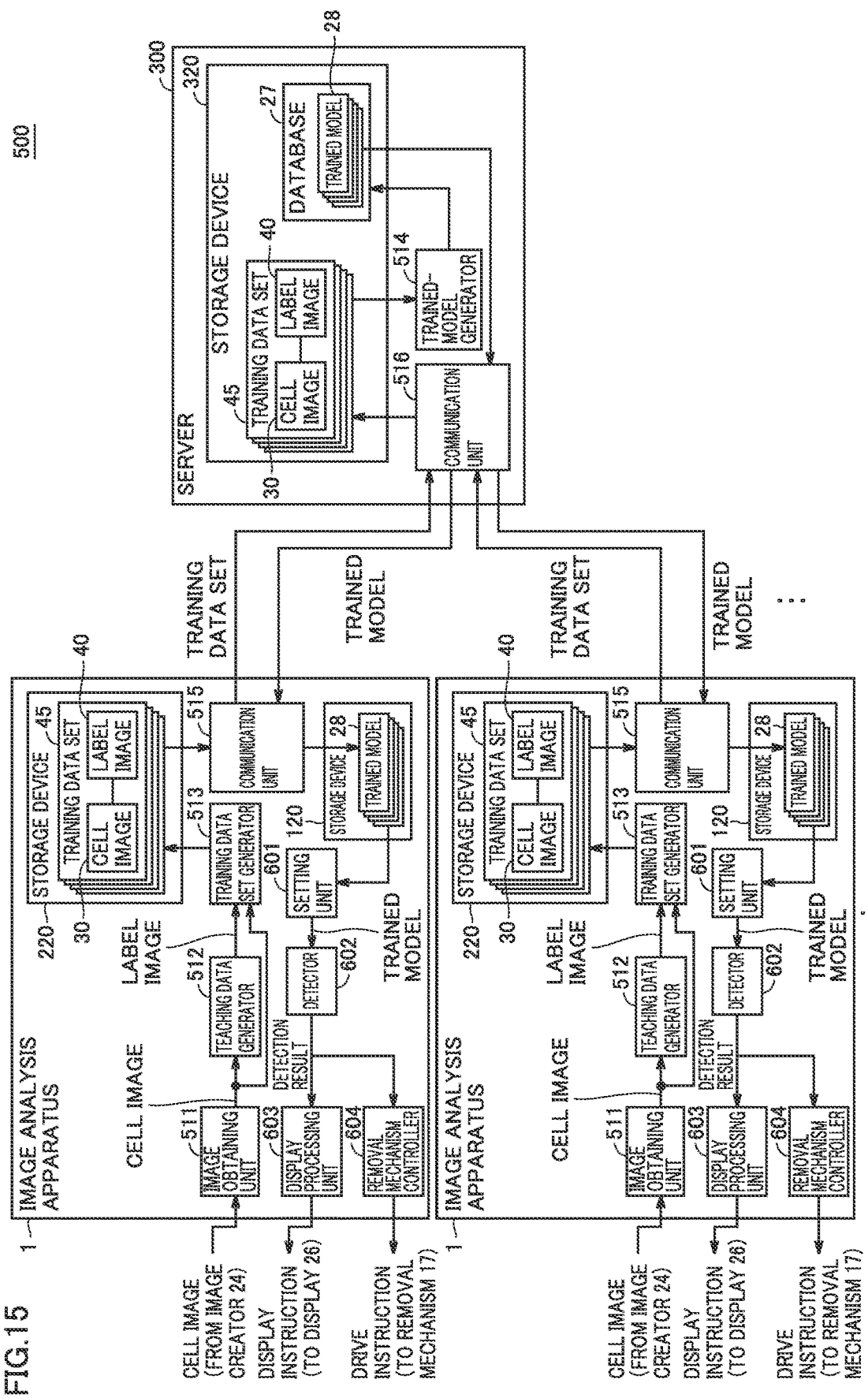
FIG. 15 is a diagram showing an exemplary functional configuration of the cell image analysis system according to the second embodiment.

A functional configuration of cell image analysis system 500 will be described with reference to FIG. 15. FIG. 15 is a diagram showing an exemplary functional configuration of cell image analysis system 500.

As shown in FIG. 15, cell image analysis system 500 includes a plurality of cell image analysis apparatuses 1 and server 300.

Cell image analysis apparatus 1 includes image obtaining unit 511, teaching data generator 512, training data set generator 513, a communication unit 515, setting unit 601, detector 602, display processing unit 603, and removal mechanism controller 604 as functional modules. Server 300 includes trained-model generator 514 and a communication unit 516 as functional modules.

Since the functional configuration other than communication units 515 and 516 is as described with reference to FIG. 4, description thereof will not be repeated below.

Communication unit 515 of cell image analysis apparatus 1 serves as a communication driver for control of communication interface 104 (or communication interface 204) described above. Communication unit 515 realizes communication with server 300. Communication unit 515 sends training data sets 45 accumulated in storage device 220 to server 300. Training data set 45 may be transmitted to server 300 each time it is generated, based on accumulation of a prescribed number of training data sets 45, or based on an operation by a user.

Preferably, training data set 45 is selected by an observer and then transmitted to server 300. More specifically, cell image analysis apparatus 1 shows collected training data sets 45 in a list. The observer checks training data sets 45 shown in the list, selects training data set 45 to be transmitted, and then performs an operation to carry out transmission. Communication unit 515 of cell image analysis apparatus 1 transmits selected training data set 45 to server 300 based on acceptance of the operation to carry out transmission.

Communication unit 516 of server 300 serves as a communication driver for control of a communication interface 304 (see FIG. 16) which will be described later. Communication unit 516 receives training data sets 45 from cell image analysis apparatuses 1 and has a storage device 320 successively store received training data sets 45. Thereafter, trained-model generator 514 carries out machine learning using training data sets 45 collected from cell image analysis apparatuses 1. The generated trained model is stored in database 27 in storage device 320.

Communication unit 516 of server 300 obtains trained model 28 designated to be downloaded from database 27 based on reception of an instruction to download trained model 28 from cell image analysis apparatus 1. Thereafter, communication unit 516 of server 300 transmits obtained trained model 28 to cell image analysis apparatus 1 from which the download instruction has been transmitted.

Communication unit 515 of cell image analysis apparatus 1 has storage device 120 store trained model 28 received from server 300.

A form of implementation of each functional module is not limited to the example shown in FIG. 15. By way of example, teaching data generator 512 and training data set generator 513 may be implemented in server 300 rather than in cell image analysis apparatus 1.

<10. Hardware Configuration of Server 300>

Figure 16:
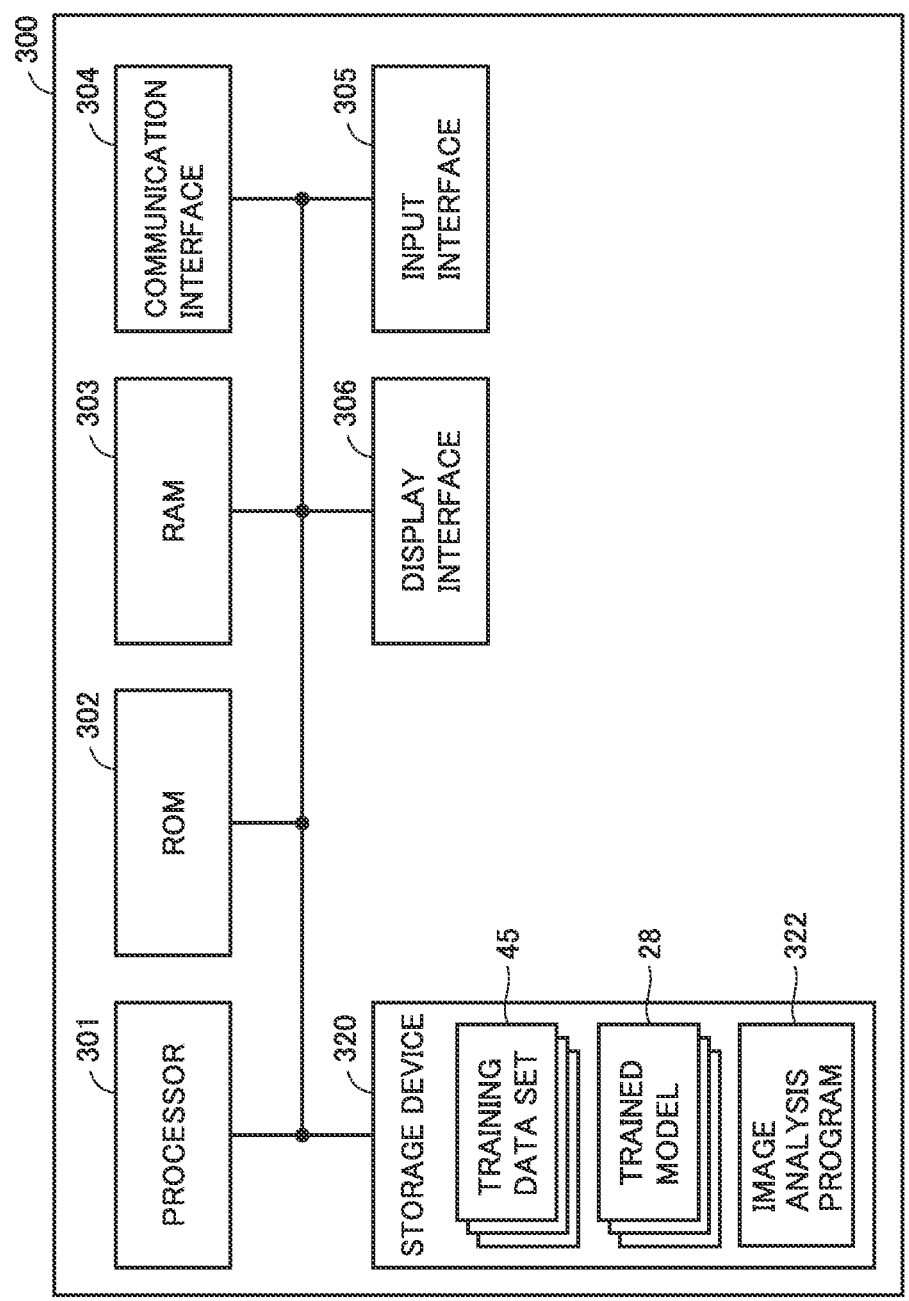
FIG. 16 is a block diagram showing a main hardware configuration of a server according to the second embodiment.

An exemplary hardware configuration of server 300 will be described with reference to FIG. 16. FIG. 16 is a block diagram showing a main hardware configuration of server 300.

Server 300 includes a processor 301, a ROM 302, a RAM 303, communication interface 304, an input interface 305, a display interface 306, a microscope interface 307, and storage device 320. Such hardware is the same as the hardware of control device 20 and as described with reference to FIG. 9 above. Therefore, only difference from control device 20 will be described below.

Storage device 320 is implemented, for example, by a storage medium such as a hard disk or a flash memory. Storage device 320 stores training data sets 45 collected from cell image analysis apparatus 1, trained model 28 generated from training data sets 45, and an image analysis program 322 for performing various types of processing relating to training processing. Image analysis program 322 includes a generation program for generating a training data set.

Image analysis program 322 may be provided as being incorporated in a part of any program, rather than a single program alone. In this case, processing according to the present embodiment is performed in cooperation with any program. Even such a program not including some modules does not depart from the gist of image analysis program 322 according to the present embodiment. A part or the entirety of functions provided by image analysis program 322 may be performed by dedicated hardware. Cell image analysis apparatus 1 and server 300 may execute image analysis program 322 in cooperation.

<11. Summary of Second Embodiment>

As set forth above, in the second embodiment, server 300 collects training data sets 45 from cell image analysis apparatuses 1 and generates a trained model from collected training data sets 45. Since such a scheme for server 300 to collect training data sets 45 from cell image analysis apparatuses 1 is provided, a large number of training data sets 45 can readily be collected.

Normally, a high-spec PC is required for machine learning. As the function for machine learning is implemented in server 300, reduction in cost for cell image analysis apparatus 1 on a user side can be achieved.

It should be understood that the embodiments disclosed herein are illustrative and non-restrictive in every respect. The scope of the present invention is defined by the terms of the claims rather than the description above and is intended to include any modifications within the scope and meaning equivalent to the terms of the claims.

REFERENCE SIGNS LIST 1 cell image analysis apparatus; 10 microscope; 11 light source; 12 image sensor; 13 culture plate; 14 cell colony; 15 reference light; 16 object light; 17 removal mechanism; 20 control device; 21 imaging controller; 22 hologram data storage; 23 phase information calculator; 24 image creator; 25 input portion; 26 display; 27 database; 27A, 27C identification information; 27B information on date and time of creation; 27D identified object information; 28 trained model; 30, 33, 35 cell image; 31 removal target; 37 subtraction image; 39, 40, 84 label image; 40A removal target region; 40B non-removal target region; 45 training data set; 50 model generation device; 51 training processing unit; 60 cell image analyzer; 70 multi-layered network; 71 convolutional layer; 80, 85 display result; 81 marker; 86, 87, 88 image area; 101, 201, 301 processor; 102, 202, 302 ROM; 103, 203, 303 RAM; 104, 204, 304 communication interface; 105, 205, 305 input interface; 106, 206, 306 display interface; 107, 207, 307 microscope interface; 120, 220, 320 storage device; 122 control program; 222, 322 image analysis program; 300 server; 500 cell image analysis system; 511 image obtaining unit; 512 teaching data generator; 513 training data set generator; 514 trained-model generator; 515, 516 communication unit; 601 setting unit; 602 detector; 603 display processing unit; 604 removal mechanism controller

The invention claimed is:

1. A cellular image analysis apparatus capable of generating teaching data to be used for machine learning, the cellular image analysis apparatus comprising:
   an image obtaining unit that obtains a first cellular image of an object that includes a removal target, the first cellular image being obtained by a microscope for observation of a cell;
   a teaching data generator that specifies a removal target region of the first cellular image that includes an image of the removal target within the first cellular image by performing predetermined image processing on the first cellular image and generates as the teaching data for machine learning, a label image that represents a location of the removal target region within the first cellular image; and
   a training data set generator that generates a set of the first cellular image and the label image as a first training data set to be used for the machine learning.

2. The cellular image analysis apparatus according to claim 1, wherein
   the image obtaining unit further obtains a second cellular image obtained by the microscope after removal of the removal target from the object, and
   the predetermined image processing includes specifying the removal target region based on a result of comparison between the first cellular image and the second cellular image.

3. The cellular image analysis apparatus according to claim 2, wherein
   the predetermined image processing includes specifying the removal target region based on a subtraction image obtained by subtracting the second cellular image from the first cellular image.

4. The cellular image analysis apparatus according to claim 2, wherein the image obtaining unit obtains the second cellular image in response to sensing a removal operation by the microscope to remove the removal target.

5. The cellular image analysis apparatus according to claim 1, comprising:
a trained-model generator that carries out machine learning using a plurality of training data sets, including the first training data set, generated by the training data set generator and generates a trained model for identifying the removal target within an image; and
a detector that detects the removal target region in an input image input to the cellular image analysis apparatus based on the trained model.

6. The cellular image analysis apparatus according to claim 5, wherein
machine learning carried out by the trained-model generator includes transfer learning using as an initial model, a part or entirety of the trained model trained in advance.

7. The cellular image analysis apparatus according to claim 5, further comprising:
a storage device that stores a plurality of trained models generated by the trained- model generator; and
an input portion that accepts a selection operation to select one trained model from among the plurality of trained models, wherein
the detector detects the removal target region in the input image based on the trained model selected by the selection operation.

8. The cellular image analysis apparatus according to claim 5, further comprising:
a display; and
a display processing unit that causes the display to show the removal target region detected by the detector as being superimposed on the input image.

9. The cellular image analysis apparatus according to claim 5, comprising a removal mechanism controller that controls a removal mechanism of the microscope to remove the removal target based on a result of detection of the removal target region detected by the detector.

10. The cell removing apparatus of claim 1,
wherein the teaching data generator generates the label image of the first training data set without manual labeling of the first cellular image.

11. A cell removing apparatus capable of generating teaching data to be used for machine learning, the cell removing apparatus comprising:
a microscope for providing an observable cellular image of an object for observation by a user and to generate a corresponding first cellular image of the object;
a removal mechanism that removes a removal target from the object represented in a predetermined region within the observable cellular image;
a teaching data generator that specifies the predetermined region within the observable cellular image as a removal target region and generates as the teaching data for machine learning, a label image that represents a location of the removal target region within the first cellular image; and
a training data set generator that generates a set of the first cellular image and the label image as a first training data set to be used for the machine learning.

12. The cell removing apparatus of claim 11, wherein the predetermined region within the observable cellular image is at the center of the observable cellular image.

13. The cell removing apparatus of claim 11, wherein the observable cellular image is a through-the-lens image.

14. A cell removing apparatus according to claim 13,
wherein the image obtaining unit further obtains a second cellular image obtained by the microscope after removal of the removal target by the removal mechanism, and
wherein the predetermined image processing includes specifying the removal target region based on a result of comparison between the first cellular image and the second cellular image.

15. The cell removing apparatus of claim 11, wherein the object is moveable or an imaging portion is moveable to include the removal target in the predetermined region.

16. The cell removing apparatus of claim 11,
wherein the removal mechanism is configured to remove the removal target in response to an acceptance of a removal operation performed by the user, and
wherein the first cellular image is obtained at the time of or immediately before the acceptance of the removal operation.

17. The cell removing apparatus of claim 11,
wherein the teaching data generator generates the label image of the first training data set without manual labeling of the first cellular image.

18. A method comprising:
receiving a cellular image and a label image that represents a location of a removal target region within the cellular image;
generating, by carrying out machine learning using the received cellular image and label image, a trained model that uses the cellular image as an input image and provides an image that represents a location of a removal target region within the input image as an output image; and
transmitting the generated trained model to a cellular image analysis apparatus.

19. The cell removing apparatus of claim 18,
wherein the cellular image and the label image from a training data set for the machine learning, and
wherein the label image is generated without manual labeling of the cellular image.

20. A method of generating teaching data to be used for machine learning, the method comprising:
obtaining a cellular image of an object that includes a removal target, the cellular image being obtained by a microscope for observation of a cell;
specifying a removal target region of the cellular image that includes an image of the removal target within the cellular image by performing predetermined image processing on the cellular image and
generating as the teaching data for machine learning, a label image that represents a location of the removal target region within the cellular image; and
generating a set of the cellular image and the label image as a training data set to be used for the machine learning.

21. The cell removing apparatus of claim 20, wherein the teaching data generator generates the label image of the first training data set without manual labeling of the cellular image.

22. The method of claim 20, wherein the location of the removal target region represented by the label image is generated by a comparison of the cellular image of the first training data set with a corresponding cellular image taken by the microscope after the removal target has been removed from the object.

23. A cell removing apparatus, comprising:
an image analysis apparatus according to claim 1; and
a removal mechanism configured to remove the target region identified via the machine learning.

24. A cell removing apparatus according to claim 23, wherein the image obtaining unit further obtains a second cellular image obtained by the microscope after removal of the removal target by the removal mechanism, and
wherein the predetermined image processing includes specifying the removal target region based on a result of comparison between the first cellular image and the second cellular image.

\* \* \* \* \*